United States Patent
Ko

(10) Patent No.: US 11,351,218 B2
(45) Date of Patent: Jun. 7, 2022

(54) **COMPOSITION FOR PREVENTING OR TREATING GLIOBLASTOMA COMPRISING *PLATYCODON GRANDIFLORUM* A. DE CANDOLLE, *SCUTELLARIA BAICALENSIS*, *PHELLODENDRON AMURENSE* RUPRECHT OR *RUBUS COREANUS***

(71) Applicant: University-Industry Cooperation Group of Kyung Hee University, Gyeonggi-do (KR)

(72) Inventor: Seong-Gyu Ko, Seoul (KR)

(73) Assignee: University-Industry Cooperation Group of Kyung Hee University, Gyeonggi-do (KR)

( * ) Notice: Subject to any disclaimer, the term of this patent is extended or adjusted under 35 U.S.C. 154(b) by 177 days.

(21) Appl. No.: 16/788,520

(22) Filed: Feb. 12, 2020

(65) Prior Publication Data
US 2020/0345802 A1  Nov. 5, 2020

(30) Foreign Application Priority Data

Feb. 12, 2019 (KR) .................. 10-2019-0016297
Apr. 18, 2019 (KR) .................. 10-2019-0045700

(51) Int. Cl.
*A61K 36/539* (2006.01)
*A61K 36/346* (2006.01)
*A61K 36/73* (2006.01)
*A61K 36/756* (2006.01)

(52) U.S. Cl.
CPC .......... *A61K 36/539* (2013.01); *A61K 36/346* (2013.01); *A61K 36/73* (2013.01); *A61K 36/756* (2013.01); *A61K 2236/331* (2013.01); *A61K 2236/333* (2013.01)

(58) Field of Classification Search
CPC .............. A61K 2300/00; A61K 36/346; A61K 36/539; A61K 36/73; A61K 36/756; A61K 2236/331; A61K 2236/333
See application file for complete search history.

(56) References Cited

U.S. PATENT DOCUMENTS 7,931,922 B2 * 4/2011 Newmark .............. A61K 36/53
424/756

FOREIGN PATENT DOCUMENTS

KR      2005/0113290 A    12/2005
KR      10-2012-017197    10/2012

OTHER PUBLICATIONS

Kanderi T, Gupta V. "Glioblastoma Multiforme", StatPearls, StatPearls Publishing (Treasure Island, FL); Jan. 2021. [Updated Jul. 7, 2021], 7 pages (PMID: 32644380). (Year: 2021).*
Xu et al "Effects of Platycodin D on Proliferation, Apoptosis and PI3K/Akt Signal Pathway of Human Glioma U251 Cells" Molecules vol. 19, pp. 21411-21423, 2014.
Gong et al "STAT3 Down Regulates LC3 to Inhibit Autophagy and Pancreatic Cancer Cell Growth" Oncotarget vol. 5, pp. 2529-2541, 2014.
Scheck et al "Anticancer Activity of Extracts Derived from the Mature Roots of *Scutellaria baicalensis* on Human Malignant Brain Tumor Cells" BMC Complementary and Alternative Medicine vol. 6, pp. 1-9, 2006.
Jeon et al "Platycodin D, a Bioactive Component of *Platycodon grandiflorum*, Induces Cancer Cell Death Associated with Extreme Vacuolation" Animal Cells and Systems vol. 23, pp. 118-127, 2019.

* cited by examiner

*Primary Examiner* — Aaron J Kosar
(74) *Attorney, Agent, or Firm* — Cesari & McKenna, LLP

(57) ABSTRACT

The present invention relates to an extract of at least any one selected from the group consisting of *Platycodon grandiflorum*, *Scutellaria baicalensis*, *Phellodendron amurense* Ruprecht, and *Rubus coreanus*, or a fraction thereof; and to a use of the same for prevention, improvement, or treatment of glioblastoma multiforme.

9 Claims, 26 Drawing Sheets

Specification includes a Sequence Listing.

COMPOSITION FOR PREVENTING OR TREATING GLIOBLASTOMA COMPRISING *PLATYCODON GRANDIFLORUM* A. DE CANDOLLE, *SCUTELLARIA BAICALENSIS*, *PHELLODENDRON AMURENSE* RUPRECHT OR *RUBUS COREANUS*

CROSS REFERENCE TO RELATED APPLICATIONS

This application claims priority to Korean Application No. 10-2019-0016297, filed on Feb. 12, 2019, and Korean Application No. 10-2019-0045700, filed on Apr. 18, 2019, the contents of both prior applications being hereby incorporated by reference in their entirety.

TECHNICAL FIELD

The present invention relates to an extract of at least any one selected from the group consisting of *Platycodon grandiflorum, Scutellaria baicalensis, Phellodendron amurense* Ruprecht, and *Rubus coreanus*, or a fraction thereof; and to a use of the same for prevention, improvement, or treatment of glioblastoma multiforme.

BACKGROUND ART

Glioblastoma multiforme (hereinafter, GBM) refers to the most malignant glioma (Grade IV by the WHO classification) among primary brain cancers, and it is known to have a very poor prognosis. The standard treatment for patients with GBM includes surgical resection, radiation therapy, and chemotherapy using temozolomide. However, in the case of temozolomide, the treatment is only effective for some patients and the average survival rate of GBM patients by the treatment is only 14 months, and thus, the development of a more effective treatment is imperative. In order to develop an effective treatment for treating patients with GBM, it is necessary to study through understanding of various molecular mechanisms affecting the growth of GBM.

Meanwhile, *Platycodon grandiflorum* (PG), which is well known as balloon flower, is also called *Platycodon grandiflorum* root. It is an herbal medicine material prepared by removing the roots or periderms of *Platycodon grandiflorum* A. De Candolle of the family Campanulaceae, and is known to have a slight odor, a bitter taste, and a very mild property. *Platycodon grandiflorum* acts on the lungs and exhibits the effects of treating symptoms of severe cough, production of heavy phlegm, and uncomfortable breathing, while capable of stopping a cough and removing phlegm. Additionally, it is also used when there is generalized edema due to inability to urinate well and when the amount of urine is small.

Therefore, it is prescribed and used for sore throat, coughs due to colds, phlegm, stuffy nose, asthma, bronchitis, pleurisy, headache, chills, tonsillitis, etc. An expectorant action, a cholesterol-lowering action, a suppression of an improved bacteriostatic action, etc. have been reported as pharmacological actions.

The Platycodin D (PD) isolated from PG is known to interfere with numerous biological processes associated with apoptosis, inflammation, oxidative stress, and hepatotoxicity.

*Scutellaria baicalensis* refers to an herbal medicine material prepared using the roots of *Scutellaria baicalensis* GEORGE, which is a perennial herbaceous plant of the family Lamiaceae. In herbal medicine, its roots are used as antipyretic, diuretic, antidiarrheic, cholagogue, and antiphlogistic agents.

*Phellodendron amurense* Ruprecht refers to a bark of an Amur cork tree, which is used as an herbal medicine material, and it is also called "hwang-kyeong-pi". The *Phellodendron amurense* Ruprecht is used as a medicinal material by peeling off the trunk of the tree to remove the rough bark or slicing and drying the peeled bark in the sun. The *Phellodendron amurense* Ruprecht is known to have a hypoglycemic action, prevent the growth of *Streptococcus pneumoniae, Mycobacterium tuberculosis, Staphylococcus*, etc., and to have a bactericidal action of these bacteria.

Additionally, *Rubus coreanus* is a plant belonging to the family Rosaceae, from which dark red fruits are harvested in early summer and used as food. In herbal medicine, *Rubus coreanus* is known as a tonic, an aphrodisiac, and an herbal medicine material that protects the liver.

SUMMARY

The present inventors have made extensive efforts to discover an herbal medicine material that inhibits the growth of glioblastoma multiforme (GBM), and as a result, they have confirmed that *Platycodon grandiflorum, Scutellaria baicalensis, Phellodendron amurense* Ruprecht, or *Rubus coreanus* has an effect of inhibiting the growth of GBM, thereby completing the present invention.

An object of the present invention is to provide a pharmaceutical composition for prevention or treatment of glioblastoma multiforme (GBM), including an extract of at least any one selected from the group consisting of *Platycodon grandiflorum, Scutellaria baicalensis, Phellodendron amurense* Ruprecht, and *Rubus coreanus*, or a fraction thereof as an active ingredient.

Another object of the present invention is to provide a method for prevention or treatment of GBM, including administering the above composition to a subject.

Still another object of the present invention is to provide a food composition for prevention or improvement of GBM, including an extract of at least any one selected from the group consisting of *Platycodon grandiflorum, Scutellaria baicalensis, Phellodendron amurense* Ruprecht, and *Rubus coreanus*, or a fraction thereof as an active ingredient.

Still another object of the present invention is to provide a feed composition for prevention or improvement of GBM, including an extract of at least any one selected from the group consisting of *Platycodon grandiflorum, Scutellaria baicalensis, Phellodendron amurense* Ruprecht, and *Rubus coreanus*, or a fraction thereof as an active ingredient.

Advantageous Effects

The extract of *Platycodon grandiflorum* of the present invention, a fraction thereof, or the platycodin D (hereinafter, PD) contained therein can effectively treat glioblastoma multiforme (GBM) by inducing the expression of low-density lipoprotein receptors (LDLRs) through an anti-autophagic action; and the extract of *Scutellaria baicalensis, Phellodendron amurense* Ruprecht, or *Rubus coreanus* of the present invention or a fraction thereof can effectively inhibit the growth of GBM by inhibiting the expression of receptor tyrosine kinase (Ax1). Therefore, the platycodin D contained in a *Platycodon grandiflorum* extract as well as an extract of *Platycodon grandiflorum, Scutellaria baicalensis*,

*Phellodendron amurense* Ruprecht, or *Rubus coreanus* or a fraction thereof can be used for the prevention, improvement, or treatment of GBM.

BRIEF DESCRIPTION OF DRAWINGS

FIG. 2A shows the results in which U87MG and U373MG cells were incubated along with platycodin D (PD) for 24 hours with different concentrations of PG extracts; and FIG. 2B shows the results in which the levels of LC3B and SQSTM1 were assessed by immunoblot analysis after GBM cells were treated with PG (500 μg/mL) over a certain time period (3 hours, 6 hours, 12 hours, and 24 hours). GAPDH was used as a loading control.

FIG. 3A shows the results in which GBM cells were incubated with PD (0 μM to 10 μM) for 24 hours. FIG. 3B shows the results in which GBM cells were treated with PD (10 μM) for 3 hours to 24 hours. The expression of LC3B and SQSTM1 was confirmed by immunoblot analysis. FIG. 3C shows the results in which relative SQSTM1 mRNA levels were analyzed by RT-PCR in GBM cells treated with PD (5 μM and 10 μM) for 24 hours. GAPDH was used as a loading control.

FIG. 6A shows the results in which cells were treated with different doses of PD (0 μM, 5 μM, 10 μM, and 20 μM) for 48 hours and the relative cell viability was determined by WST1 assay. Data shown represent the means of quintuplicate measurements which were repeated three times. The results are presented as a percentage of control (means±SD). FIG. 6B shows the results in which GBM cells were treated with DMSO or PD (10 μM) for 24 hours and cell morphology was observed under an optical microscope.

FIG. 7A shows the results in which cells were treated with different concentrations of PD for 24 hours and then the levels of PARP, capase-3, BCL-2, and BAX were assessed by immunoblot analysis. GAPDH was used as a loading control. FIG. 7B shows the results in which cells were incubated with PD (10 μM and 20 μM) in the presence or absence of z-VAD-fmk (50 μM) for 48 hours, and the relative cell viability was measured by WST1 assay. Data shown represent the means of quintuplicate measurements which were repeated three times. The results are presented as a percentage of control (means±SD).

FIGS. 9A and 9B show the results in which indicated cells were treated with different concentrations of PG or PD for 48 hours and cell viability was measured by WST1 assay. Data shown represent the means of quintuplicate measurements which were repeated three times. The results are presented as a percentage of control (means±SD). FIG. 9C shows the results in which cells were treated with PG (500 μg/mL) or PD (10 μM) for 24 hours and the morphology was directly observed under an optical microscope.

FIGS. 10A to 10C show the results in which cells were treated with PD (0 μM, 0.5 μM, 1 μM, 5 μM, and 10 μM) for 24 hours. The immunoblot analyses for p-ULK1 (Ser757), ULK1, p-S6K (Thr389), p-AKT (Ser473), ERK2, $_p$-ERK, p-JNK1, Beclin, and ATG7 were performed using lysates from GBMs. FIG. 10D the shows results in which cells were pre-incubated along with PD98059 (50 μM) for 30 minutes and then treated with PD (10 μM) for 24 hours. Total protein extracts were analyzed by immunoblot analyses for p-ERK, LC3B, and SQSTM1. GAPDH was used as an internal control.

FIG. 15A shows the results in which cellular cholesterol distribution was determined by filipin staining FIG. 15B shows the results in which free cholesterol and cholesteryl ester were measured by a cholesterol assay kit. Total cholesterol levels are expressed in cholesterol (μg) per protein (mg) of cell lysate and are shown as means±SD from two independent experiments.

FIG. 16A shows the results in which relative expression of LDLR was detected by immunoblot analysis. FIG. 16B shows the results in which all cells were treated with PD (5 μM and 10 μM) or U18666a (1 μM) for 24 hours and then the protein levels of LDLR were assessed by western blot analysis. GAPDH was used as a loading control. FIG. 16C shows the results in which cells were treated with DMSO, PD (10 μM), or U18666a (1 μM) for 24 hours and the levels of cell-surface LDLR were assessed by flow cytometry analysis. A representative histogram shows the intensity of LDLR staining. FIG. 16D shows the results in which relative LDLR mRNA levels were analyzed by RT-PCR in GBM cells treated with PDM (10 μM) or U18 (1 μM) for 24 hours. GAPDH was used as a loading control.

FIG. 18A shows the results in which cells were first treated with PD (10 μM) for 24 hours and subsequently exposed to MβCD (100 μM) for 48 hours. FIG. 18B shows the results in which the expressions of LC3B, SQSTM1, and pro/active CTSB were detected by immunoblot analysis. GAPDH was used as a loading control. FIG. 18C shows the results in which cells transiently expressing GFP-LC3 (green) were exposed to PD (10 μM) and MβCD (100 μM) for 48 hours and then stained with LysoTracker (red). The merged images (yellow) show an overlap between GFP-LC3 and LysoTracker (yellow).

FIG. 19A shows the results in which cells were treated with PD (10 μM) in the presence or absence of MβCD (100 μM) for 72 hours and cell viability was measured by WST1 assay. FIG. 19B shows the results in which cells were treated with PD (10 μM or 20 μM) in the presence or absence of MβCD (100 μM) for 7 days and processed for clonogenic assay to measure a proliferation ability. Data shown represent the means of quintuplicate measurements which were repeated three times. The results are presented as a percentage of control (means±SD).

FIG. 20A shows the results in which cells infected with shNS or shLDLR lentiviral vectors were first treated with PD (5 μM or 10 μM) for 24 hours. The expressions of LDLR, LC3B, SQSTM1, and pro/active CTSB were detected by immunoblot analysis. GAPDH was used as a loading control. FIG. 20B shows the results in which each cell was treated with PD (10 μM or 20 μM) and then subjected to WST1 assay. Data shown represent the means of quintuplicate measurements which were repeated three times. The results are presented as a percentage of control (means±SD).

BEST MODE FOR CARRYING OUT THE INVENTION

Figure 1:
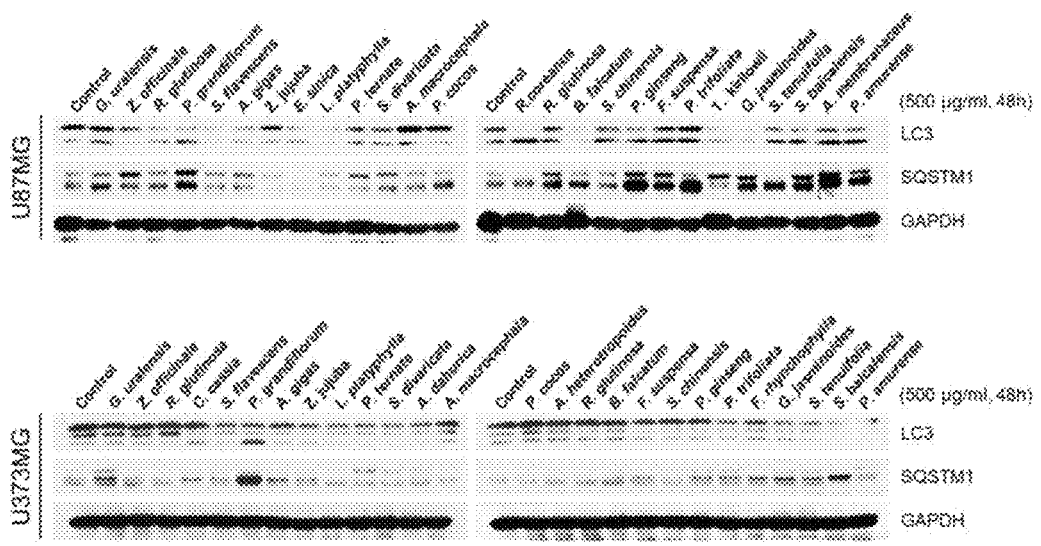
FIG. 1 shows the results of screening various kinds of herbal medicines for the identification of novel autophagy inhibitors. The effects of 26 kinds of herbal medicines, which influence the expression of autophagy-related proteins (LC3B and SQSTM1/p62) in total cell lysates from U87MG and U373MG cells, were evaluated at a concentration of 500 μg/mL for 48 hours by western blot analysis. GAPDH was used as a loading control.
Figure 2A:
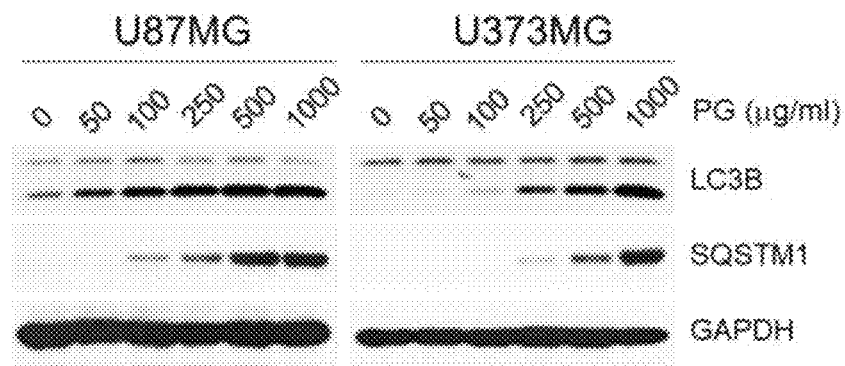
FIGS. 2A and 2B show the results that an extract of *Platycodon grandiflorum* (PG) increases the levels of LC3-II and p62.
Figure 2B:
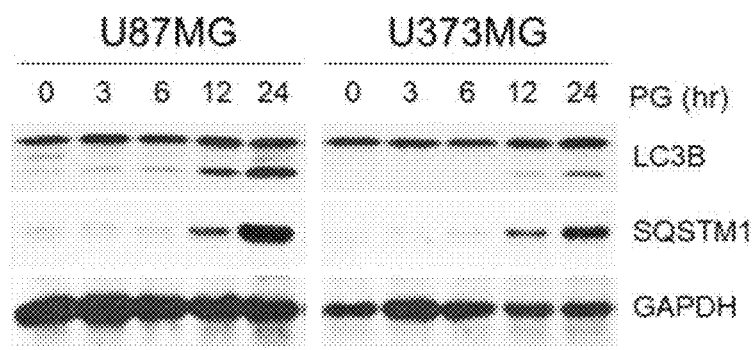
Figure 3A:
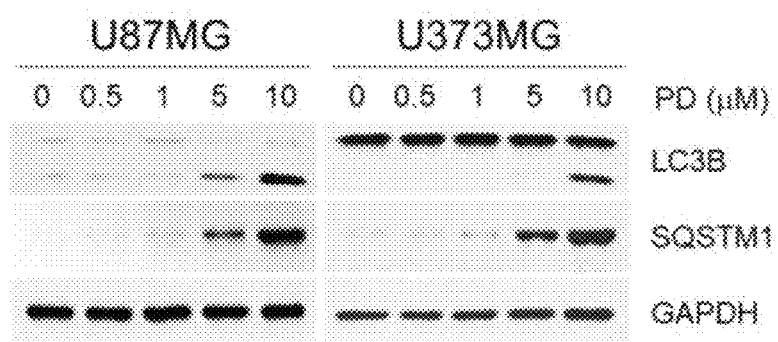
FIGS. 3A to 3C show the results that PD inhibits autophagic flux in GBM cells.
Figure 3B:
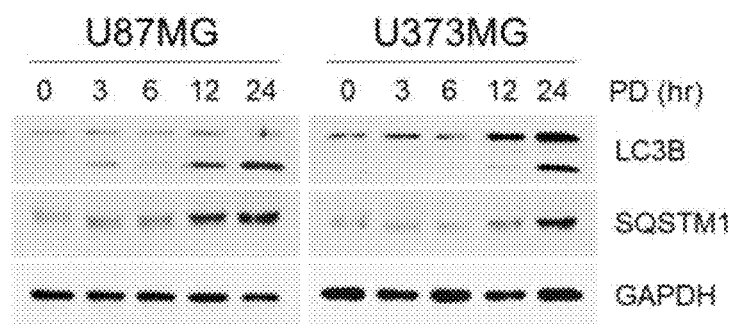
Figure 3C:
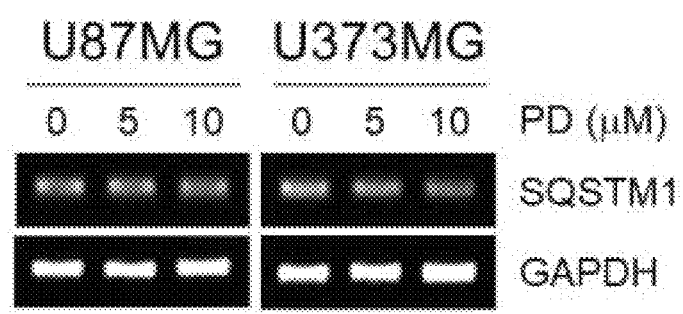
Figure 4:
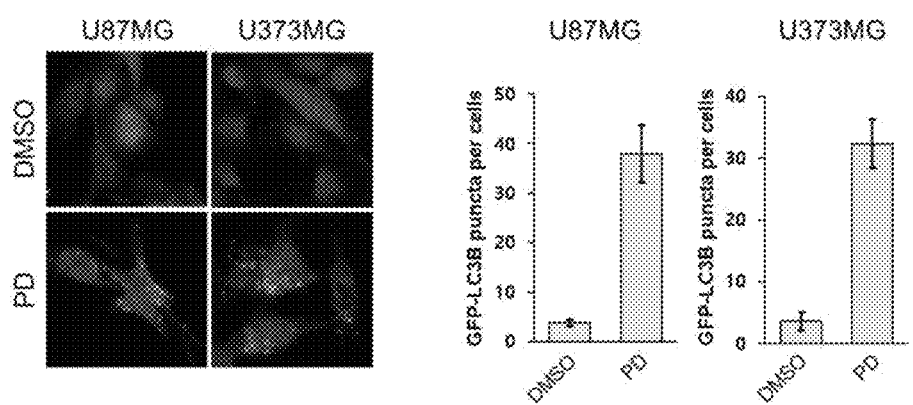
FIG. 4 shows the results that PD increases GFP-LC3B puncta in GBM cells. The cells transiently expressing GFP-LC3 (green) were treated with DMSO or PD (10 μM) for 24 hours and analyzed by confocal microscopy. Nuclei were stained with DAPI (blue). Quantification shown on the right graph represents mean GFP-LC3B puncta per cells from three independent experiments±SD.
Figure 5:
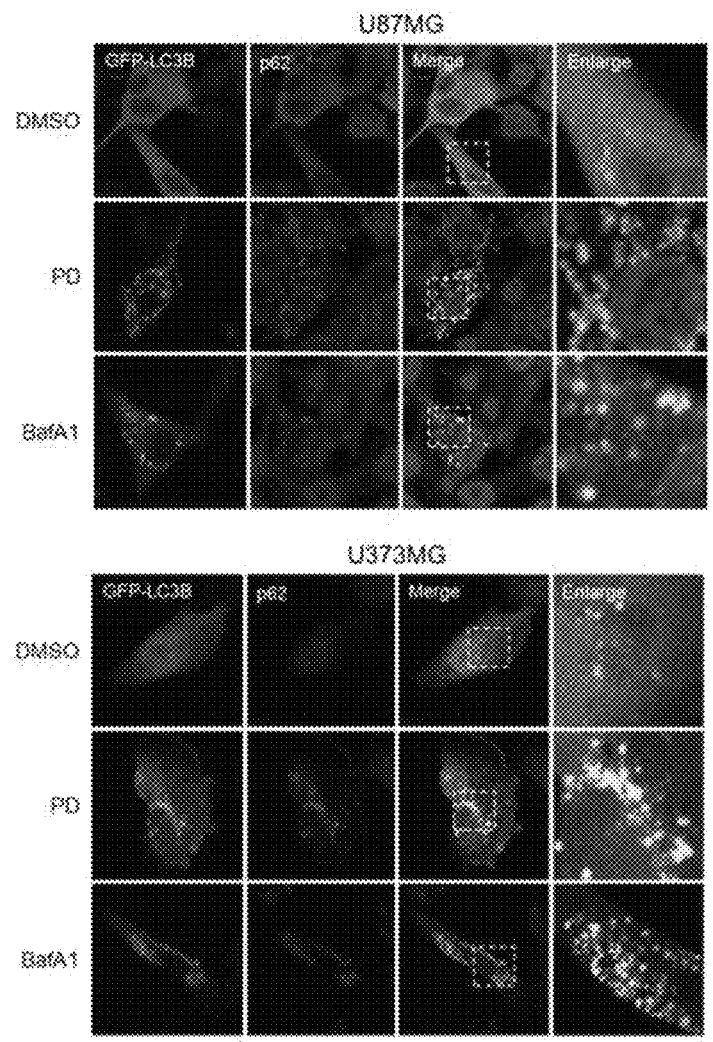
FIG. 5 shows the results that PD blocks degradation of p62 in autophagosomes. The cells expressing GFP-LC3B (green) were treated with DMSO, PD (10 μM), or BafA1 (100 μM) for 24 hours, followed by staining with an anti-SQSTM1 antibody (red) and DAPI (blue). The merged images (yellow) indicate co-localization between LC3 and p62. The panels on the right are higher-magnification images of the boxed regions.

To achieve the above objects, an aspect of the present invention provides a pharmaceutical composition for prevention or treatment of glioblastoma multiforme (GBM), which includes an extract of at least any one selected from the group consisting of *Platycodon grandiflorum*, *Scutellaria baicalensis*, *Phellodendron amurense* Ruprecht, and *Rubus coreanus*, or a fraction thereof as an active ingredient.

As used herein, the term "glioblastoma multiforme (GBM)" is a Grade IV astrocytoma which is the most malignant among the astrocytomas, in which necrotic findings are added to anaplastic astrocytoma from a histological point of view. This tumor is the most common primary brain tumor accounting for half of glioma and 15% of pediatric glioma, and it is rarely reported to occur in the cerebellum.

The term "astrocytoma" refers to a tumor that occurs in astrocytes, which are the supporting cells of the brain, and it is a brain tumor where variations generally occur most frequently.

As used herein, the term "*Platycodon grandiflorum*" refers to an herbal medicine material prepared by removing the roots or periderms of *Platycodon grandiflorum* A. De Candolle of the family Campanulaceae. *Platycodon grandiflorum* is mainly used as an herbal medicine, and in oriental medicine, it is used as a medicine for coughing, gallstones, removal of phlegm, nasal congestion, colds, tonsillitis, and sinusitis.

As used herein, the term "*Scutellaria baicalensis*" refers to an herbal medicine material prepared using the roots of *Scutellaria baicalensis* GEORGE, which is a perennial herbaceous plant of the family Lamiaceae. *Scutellaria baicalensis* usually grows in the grasslands of mountains, and it is characterized in that several stems grow in bundles, have hairs, and stems are branched. Its original root is conical and its flesh is yellow. In oriental medicine, *Scutellaria baicalensis* is used as antipyretic, diuretic, antidiarrheic, cholagogue, and antiphlogistic agents. Meanwhile, baicalin, which is a type of flavonoid contained in *Scutellaria baicalensis*, is known to have antioxidant, and anti-inflammatory effects.

As used herein, the term "*Phellodendron amurense* Ruprecht" refers to a bark of an Amur cork tree, which is used as an herbal medicine material, and it is also called "hwang-kyeong-pi". It is a deciduous broad-leaved tree that grows to a height of about 10 m, and it is characterized in that cork develops in the bark and the inner skin is yellow. In Korea, it is evenly distributed in all areas except Jeju and Jeonnam provinces and it grows in mixed forests or mountain valleys. *Phellodendron amurense* Ruprecht is used as a medicinal material by peeling off the trunk of the tree to remove the rough bark or slicing and drying the peeled bark in the sun around the summer solstice. *Phellodendron amurense* Ruprecht is known to have a hypoglycemic action, prevents the growth of *Streptococcus pneumoniae, Mycobacterium tuberculosis, Staphylococcus*, etc., and has a bactericidal action against these bacteria.

As used herein, the term "*Rubus coreanus*" refers to a plant belonging to the family Rosaceae, which is native to China. In Korea, it is mainly produced in Jeju province and southern parts of the country. Dark red fruits of *Rubus coreanus* are harvested in early summer and used as edible food. In oriental medicine, *Rubus coreanus* is known as a tonic, an aphrodisiac, and an herbal medicinal material that protects the liver.

The *Platycodon grandiflorum, Scutellaria baicalensis, Phellodendron amurense* Ruprecht, or *Rubus coreanus* can be harvested from nature, cultivated, or purchased and used by other known methods. Additionally, the *Platycodon grandiflorum* extract can be extracted from natural, hybrid, and modified plants, and from plant tissue cultures.

As used herein, the term "extract" refers to a material obtained by extraction treatment of a certain material, and specifically, it includes the extract itself and all possible formulations of the extract that can be formed using the extract (e.g., an extract liquid obtained by the extraction treatment of the present invention, a diluent or concentrate of the extract liquid, a dried product obtained by drying the extract liquid, a crude or purified product of the extract liquid, a mixture thereof, etc.).

The extract may be a single extract of *Platycodon grandiflorum, Scutellaria baicalensis, Phellodendron amurense* Ruprecht, or *Rubus coreanus*, and it may be a combined extract of two or more selected from the group consisting of *Platycodon grandiflorum, Scutellaria baicalensis, Phellodendron amurense* Ruprecht, and *Rubus coreanus*, but the extract is not limited thereto. More specifically, the extract may be an extract of *Platycodon grandiflorum* and *Scutellaria baicalensis*; an extract of *Platycodon grandiflorum* and *Phellodendron amurense* Ruprecht; an extract of *Platycodon grandiflorum* and *Rubus coreanus*; an extract of *Scutellaria baicalensis* and *Phellodendron amurense* Ruprecht; an extract of *Phellodendron amurense* Ruprecht and *Rubus coreanus*; an extract of *Scutellaria baicalensis* and *Rubus coreanus*; an extract of *Scutellaria baicalensis, Phellodendron amurense* Ruprecht, and *Rubus coreanus*; an extract of *Platycodon grandiflorum, Scutellaria baicalensis*, and *Phellodendron amurense* Ruprecht; an extract of *Platycodon grandiflorum, Scutellaria baicalensis*, and *Rubus coreanus*; an extract of *Platycodon grandiflorum, Phellodendron amurense* Ruprecht, and *Rubus coreanus*; or an extract of *Platycodon grandiflorum, Scutellaria baicalensis, Phellodendron amurense* Ruprecht, and *Rubus coreanus*.

The method for extracting the above extract is not particularly limited as long as the active ingredients in the extract obtained by the method are not destroyed or can be minimized, and the extract may be extracted according to the conventional method used in the art. Non-limiting examples of the method for extracting the above extract may include a shaking extraction method, a solvent extraction method, an ultrasonic extraction method, a cold precipitation extraction method, a filtration method, a reflux extraction method, etc., and these methods may be performed alone or in combination of two or more kinds of methods.

In the present invention, the kind of extraction solvent to be used in the above extract is not particularly limited, and any solvent known in the art may be used. Non-limiting examples of the extraction solvent may include water, a $C_1$-$C_4$ alcohol, a mixed solvent thereof, etc. and these solvents may be used alone or by mixing one or more kinds thereof. Specifically, the extraction solvent may be hot water.

Specifically, in the present invention, the extract of *Platycodon grandiflorum, Scutellaria baicalensis, Phellodendron amurense* Ruprecht, or *Rubus coreanus* may be obtained as follows. *Platycodon grandiflorum, Scutellaria baicalensis, Phellodendron amurense* Ruprecht, or *Rubus coreanus* may be extracted with a polar solvent, such as water and $C_1$-$C_4$ alcohols (e.g., methanol, ethanol, propanol, butanol, etc.), which is used in an amount of about 2- to 20-fold relative to the weight of *Platycodon grandiflorum, Scutellaria baicalensis, Phellodendron amurense* Ruprecht, or *Rubus coreanus*, and specifically in a volume of about 3- to 5-fold relative to that of *Platycodon grandiflorum, Scutellaria baicalensis, Phellodendron amurense* Ruprecht, or *Rubus coreanus*, or a mixed solvent in which these solvents are mixed in a ratio of about 1:0.1 to about 1:10 may be used as an elution solvent, but the method is not limited thereto. The extraction temperature may be in a range from 1° C. to 100° C., and specifically from 15° C. to 35° C.; the extraction period may be in a range from about 1 hour to about 10 days, and specifically 2 to 50 hours; and the extraction method may be a shaking extraction method, a hot water extraction method, a cold precipitation extraction method, a reflux cooling extraction method, an ultrasonic extraction method, or a combined method thereof, but are not limited thereto.

As used herein, the term "fraction" refers to a resulting product obtained by performing a fractionation to separate a particular component or a group of particular components from a mixture containing various components.

In the present invention, the fractionation method to obtain a fraction is not particularly limited as long as the fraction obtained therefrom exhibits an effect of inhibiting glioblastoma multiforme (GBM), and it may be performed according to a method commonly used in the art. Non-limiting examples of the fractionation method include a solvent fractionation method performed by treatment with various solvents, an ultrafiltration fractionation method performed via passage of an ultrafiltration membrane having a constant molecular weight cut-off value, a chromatographic fractionation method performed by various kinds of chromatography (manufactured for separation according to size, charge, hydrophobicity, or affinity), a combination thereof, etc.

In the present invention, the solvent type for fractionation used to obtain a fraction is not particularly limited, but any solvent known in the art may be used. Non-limiting examples of the solvent for fractionation may include polar solvents (e.g., water, distilled water, alcohol, etc.); and non-polar solvents (e.g., hexane, ethyl acetate, chloroform, dichloromethane, etc.). These solvents may be used alone or two or more kinds of these solvents may be mixed for use, but are not limited thereto. In case where alcohol is used among the above solvents for fractionation, it is preferable that a $C_1$-$C_4$ alcohol is used, but is not limited thereto.

The *Platycodon grandiflorum* extract or a fraction thereof may be contained in an amount of 0.01 wt % to 99 wt %, specifically 0.05 wt % to 90 wt %, and more specifically 0.1 wt % to 80 wt % relative to the total amount of the composition, but is not limited thereto.

The *Platycodon grandiflorum* extract or a fraction thereof may contain platycodin D, but is not limited thereto.

As used herein, the term "platycodin D" refers to a compound represented by the following Formula 1 having a formula of $C_{57}H_{92}O_{28}$, and it is a type of saponin.

dins A, C, D, and D2, and two kinds of monoacetates, and platycodin D3 have been reported as glycosides of platycodigenin.

The platycodin D may be contained in an amount of 0.01 wt % to 99 wt %, specifically 0.05 wt % to 90 wt %, and more specifically 0.1 wt % to 80 wt % relative to the total amount of the composition, but is not limited thereto.

The *Platycodon grandiflorum* extract or a fraction thereof may be one that inhibits autophagy in cancer cells, but is not particularly limited thereto.

The term "autophagy" refers to the removal of cellular wastes, degenerative proteins, or cell organelles whose life span has been completed or whose functions have been deteriorated due to denaturation, by the cells themselves.

The inhibition of autophagy may increase the expression of low-density lipoprotein receptors (LDLRs) in cancer cells, but is not particular limited thereto.

Specifically, the inhibition of autophagy may be due to inhibition of the fusion between autophagosomes and lysosomes in the autophagy process in cancer cells, but is not particularly limited thereto.

Specifically, the increase in the expression of LDLRs may accumulate cholesterol in the lysosomes in cancer cells, but is not particularly limited thereto.

[Formula 1]

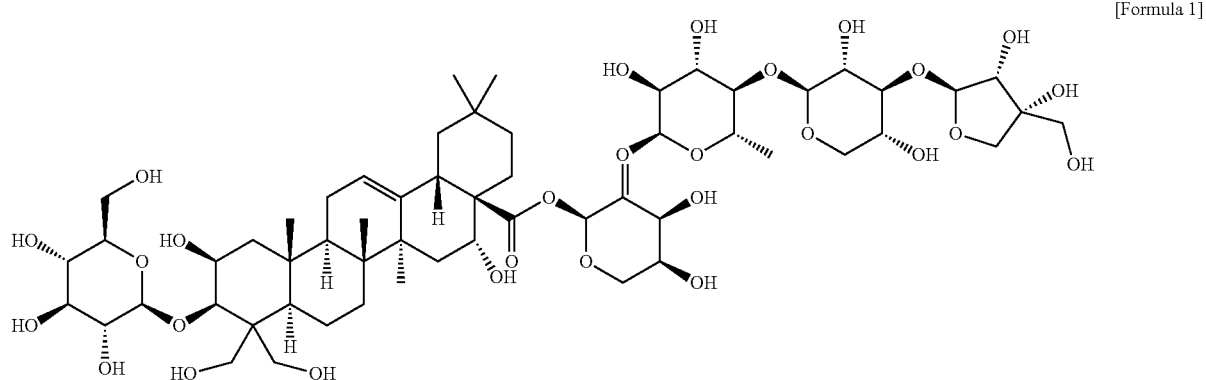

As the platycodin D, those extracted from natural products may be used, but those which are chemically synthesized may also be used, and the platycodin D to be used is not limited thereto as long as it shows the same effect as those extracted from natural products.

Specifically, in the present invention, the platycodin D may be extracted and purified from *Platycodon grandiflorum*, but is not particularly limited thereto, and the platycodin D may be extracted from various kinds of natural products other than *Platycodon grandiflorum*. The platycodin D may be isolated and purified from a *Platycodon grandiflorum* extract according to a conventional method known in the art, and it may be isolated and purified using a conventional solvent under conventional temperature and pressure conditions.

The above saponins include triterpenes and steroids as aglycones and are classified into a compound group in which, the aglycones form a glycosidic bond to a sugar moiety. Additionally, these saponins can be distinguished according to sapogenins, and among them, the *Platycodon grandiflorum* saponin belongs to pentacyclic oleanane-type triterpene saponins. Specifically, *Platycodon grandiflorum* contains about 2% of 10 or more kinds of triterpene saponins as a saponin component, and among these saponins, platyco- The pharmaceutical composition may increase the expressions of the gene and the protein of a marker associated with the inhibition of autophagy, but is not particularly limited thereto.

Specifically, the marker associated with the inhibition of autophagy may be any one selected from the group consisting of LC3-II and p62, but is not particularly limited thereto.

Figure 20A:
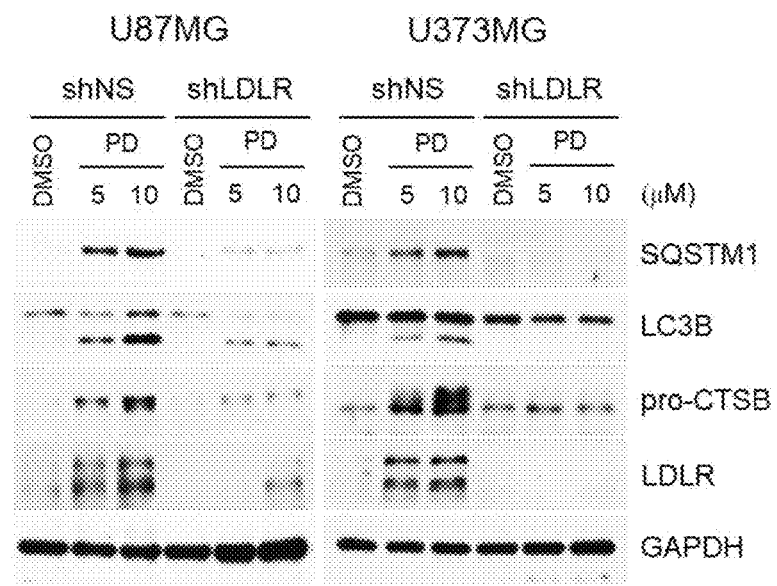
FIGS. 20A and 20B show the results that downregulation of LDLR restores inhibition of autophagy and cell viability.
Figure 20B:
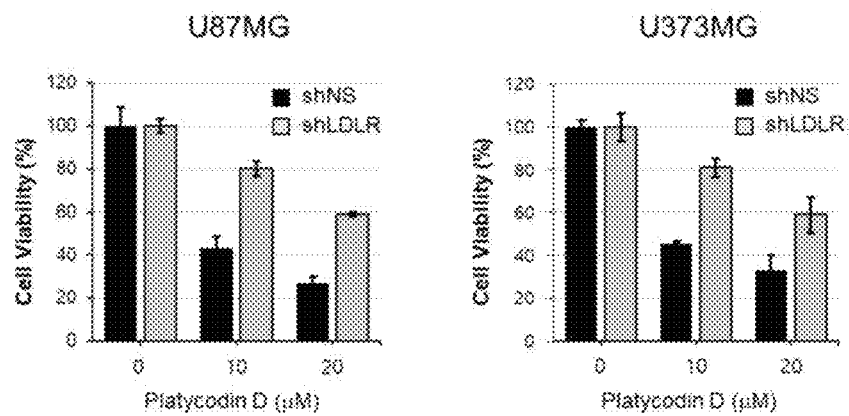
Figure 21:
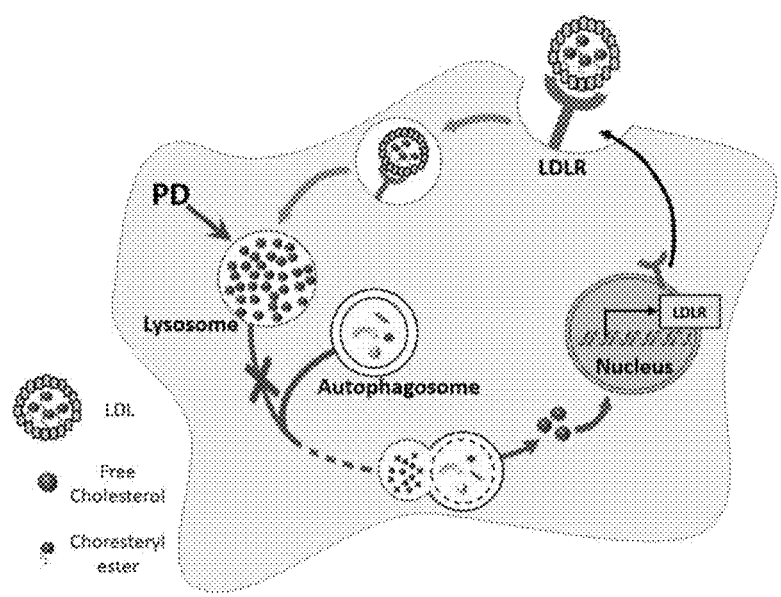
FIG. 21 shows the schematic diagram which illustrates that PD inhibits autophagy via regulation of cholesterol.

In a specific embodiment of the present invention, it was confirmed that the administration of a *Platycodon grandiflorum* extract or the platycodin D contained therein has the effects of inhibiting autophagy and reducing cell viability of glioblastoma multiforme (GBM) (FIGS. 20A and 20B).

The extract of at least any one selected from the group consisting of *Scutellaria baicalensis, Phellodendron amurense* Ruprecht, and *Rubus coreanus*, or a fraction thereof may be contained in an amount of 0.0001 wt % to 80 wt %, specifically 0.0001 wt % to 50 wt %, and more specifically 0.01 wt % to 20 wt % relative to the total amount of the composition, but is not limited thereto.

The extract of at least any one selected from the group consisting of *Scutellaria baicalensis, Phellodendron amurense* Ruprecht, and *Rubus coreanus*, or a fraction thereof may reduce the expression of the Ax1 protein in cancer cells thereby inhibiting the growth of glioblastoma multiforme (GBM), but is not particularly limited thereto.

As used herein, the term "Ax1 protein" refers to a receptor tyrosine kinase Ax1 that belongs to the Tyro3-Ax1-Mertk (TAM) receptor group, and it has recently received attention as a target protein for cancer treatment. The structure of Ax1 protein consists of two immunoglobulin-like domains and two fibronectin III domains, which are exposed outside the cell; a single-pass transmembrane domain; and a tyrosine phosphorylation domain inside the cell. Growth arrest-specific gene6 (GAS6) and protein S (PROS1) are known as ligands that induce activation by binding to Ax1 receptors.

Clinically, it has been reported that the Ax1 expression level is higher in primary and metastatic cancer compared to those in normal tissues. In addition, as the Ax1 expression becomes higher, lung cancer, pancreatic cancer, kidney cancer, colon cancer, liver cancer, esophageal cancer, glioblastoma multiforme (GBM), etc. are reported to have poor prognosis. Additionally, Ax1 is known as a protein that plays an important role in inducing intrinsic and acquired resistance to chemotherapy, immunotherapy, and molecular targeted anticancer drugs. Since the first report of study results showing that Ax1 mRNA is expressed at least twice as high in cisplatin-resistant ovarian cancer, it has been found that there is a correlation between the expression of Ax1 and anticancer drug resistance in breast cancer, colon cancer, lung cancer, etc. Recently, it has been known that the overexpression of Ax1 is the cause of the anti-cancer drug resistance mechanism against epidermal growth factor receptors (EGFR) targeted anticancer agent erlotinib in non-small cell lung cancer with mutations in the epidermal growth factor (EGF) receptors.

Specifically, the decrease in the expression of Ax1 protein may inhibit the activity of STATS, thereby inhibiting the growth of glioblastoma multiforme (GBM), but is not particularly limited thereto.

Figure 24:
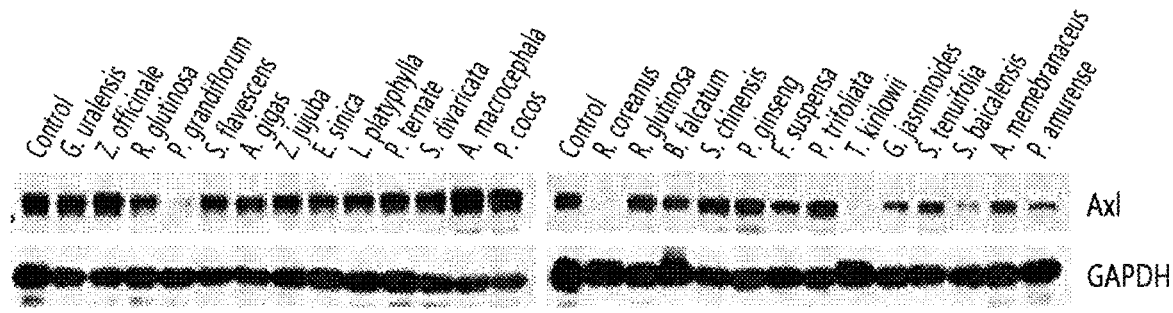
FIG. 24 shows the results in which, in order to discover herbal medicines capable of inhibiting the Ax1, water extracts of 26 kinds of herbal medicines were treated on U87MG cells (i.e., a GBM cell line) for 24 hours and then subjected to western blot to compare the expression level between Ax1 and GAPDH.
Figure 25:
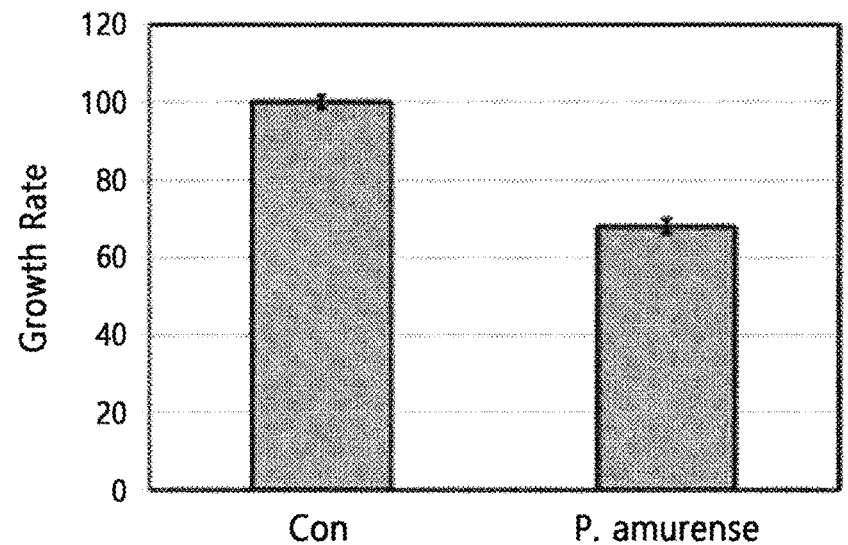
FIG. 25 shows the graph in which a *Phellodendron amurense* Ruprecht extract, which was shown to inhibit Ax1, was treated on U87MG cells (i.e., a GBM cell line) for 48 hours and then the growth of the cells was compared with the control.
Figure 26:
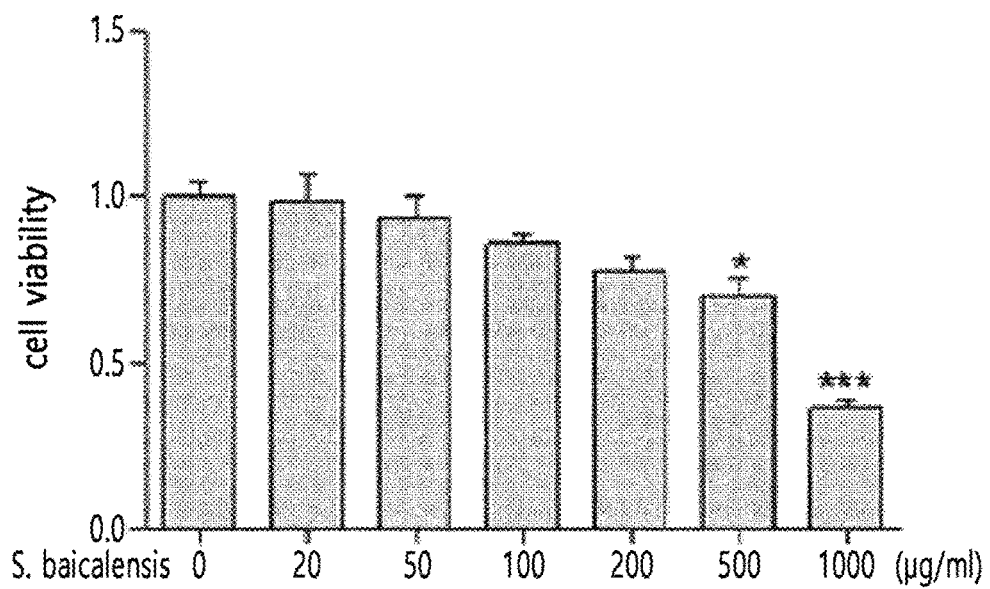
FIG. 26 shows the graph in which a *Scutellaria baicalensis* extract, which was shown to inhibit Ax1, was treated on U87MG cells (i.e., a GBM cell line) for 48 hours and then viability of the cells was compared with the control.

In a specific embodiment of the present invention, it was confirmed that the administration of an extract of *Scutellaria baicalensis, Phellodendron amurense* Ruprecht, or *Rubus coreanus* can inhibit and reduce the expression of Ax1 in glioblastoma multiforme (GBM) (FIG. 24), and in another embodiment of the present invention, it was confirmed that the growth of glioblastoma multiforme (GBM) was inhibited when GBM was grown in a cultured liquid containing an extract of *Scutellaria baicalensis* or *Phellodendron amurense* Ruprecht (FIGS. 25 and 26).

The composition may further include at least any one selected from the group consisting of a pharmaceutically acceptable salt, carrier, excipient, and diluent, but is not limited thereto.

The kind of salt is not particularly limited. However, it is preferable that the salt is in a form that is safe and effective for a subject (e.g., a mammal), but is not particularly limited thereto.

As used herein, the term "pharmaceutically acceptable" refers to a material that can be effectively used for a desired purpose without causing excessive toxicity, irritation, allergic reactions, etc. within the scope of medical judgment.

As used herein, the term "pharmaceutically acceptable salt" includes salts derived from pharmaceutically acceptable inorganic acids, organic acids, or bases. Examples of suitable acids are hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzenesulfonic acid, etc. The salts derived from suitable bases may include alkali metals (e.g., sodium, potassium, etc.), alkaline earth metals (e.g., magnesium, etc.), ammonium, etc.

The term "carrier" refers to a medium that provides a surface for attachment for proliferation and growth of microorganisms within a bioreactor. The pharmaceutically acceptable carrier is conventionally used at the time of manufacturing preparations, and it includes saline, sterile water, a Ringer's solution, buffered saline, cyclodextrin, a dextrose solution, a maltodextrin solution, glycerol, ethanol, liposomes, etc., but is not limited thereto, and may further include other conventional additives (e.g., antioxidants, buffers, etc.) as necessary. The carrier may include a non-naturally occurring carrier, but is not limited thereto.

Excipients and diluents that may be included in the pharmaceutical composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, polycaprolactone, polylactic acid, poly-L-lactic acid, mineral oil, etc.

The pharmaceutical composition may be used by formulating in the form of an oral dosage form (e.g., powders, granules, tablets, capsules, suspensions, emulsions, syrups, aerosols, etc.), preparations for external use, suppositories, and sterile injectable solutions, respectively, according to a conventional method. The carrier type may include various types of amorphous carriers, microspheres, nanofibers, etc.

In the case of formulation, the pharmaceutical composition may be prepared using the commonly used diluents or excipients (e.g., fillers, extenders, binders, humectants, disintegrants, surfactants, etc.).

Solid preparations for oral administration include tablets, pills, powders, granules, capsules, etc. These solid preparations may be prepared by mixing at least one excipient (e.g., starch, calcium carbonate, sucrose or lactose, gelatin, etc.), with the above extracts and fractions thereof. Additionally, lubricants (e.g., magnesium stearate and talc) may be used in addition to simple excipients.

Liquid preparations for oral administration include suspending agents, liquids for internal use, emulsions, syrups, etc., and various kinds of excipients (e.g., humectants, sweeteners, fragrances, preservatives, etc.) may be used, in addition to water and liquid paraffin, which are commonly used simple diluents.

Preparations for parenteral administration may include sterile aqueous solutions, non-aqueous solvents, suspensions, emulsions, lyophilized preparations, suppositories, etc.

Non-aqueous solvents and suspensions may include propylene glycol, polyethylene glycol, vegetable oils (e.g., olive oil), injectable esters (e.g., ethyl oleate), etc.

As used herein, the term "prevention" refers to all actions that inhibit or delay the onset of glioblastoma multiforme (GBM) by the administration of an extract of at least any one selected from the group consisting of *Platycodon grandiflorum, Scutellaria baicalensis, Phellodendron amurense* Ruprecht, and *Rubus coreanus* according to the present invention, a fraction thereof, an active ingredient derived therefrom, or the above composition.

As used herein, the term "treatment" refers to all actions that improve or beneficially change the symptoms of glioblastoma multiforme (GBM) by the administration of an extract of at least any one selected from the group consisting of *Platycodon grandiflorum, Scutellaria baicalensis, Phellodendron amurense* Ruprecht, and *Rubus coreanus* according to the present invention, a fraction thereof, an active ingredient derived therefrom, or the above composition.

Another aspect of the present invention provides a method for the prevention or treatment of glioblastoma multiforme (GBM), which includes administering the above pharmaceutical composition to a subject.

The terms used herein are as described above.

Since the pharmaceutical composition of the present invention exhibits an effect of preventing or treating glioblastoma multiforme (GBM), the method of the present invention including administering the above pharmaceutical composition to a subject can be effectively used for the prevention or treatment of glioblastoma multiforme (GBM).

As used herein, the term "subject" refers to all animals (e.g., rats, mice, livestock, etc., including humans), in which glioblastoma multiforme (GBM) has occurred or may occur, and in a specific embodiment, the subject may refer to a mammal including humans, but is not limited thereto.

As used herein, the term "administration" refers to introduction of the above composition to a subject in an appropriate manner.

The pharmaceutical composition of the present invention may be administered in a pharmaceutically effective amount.

As used herein, the term "pharmaceutically effective amount" refers to an amount sufficient to treat the disease at a reasonable benefit/risk ratio applicable to medical treatment, and an effective dose level may be determined according to factors, including subject type and severity, age, sex, drug activity, sensitivity to drugs, administration time, administration route and excretion rate, duration of treatment, drugs to be co-administered, and other factors well known in the medical field.

The pharmaceutical composition may be administered as an individual therapeutic agent or in combination with other therapeutic agents, and it may be administered sequentially or simultaneously with conventional therapeutic agents. Additionally, the pharmaceutical composition may be administered once or multiple times. Considering all of the above factors, it is important to administer an amount that can achieve the maximum effect in a minimal amount without side effects, and this can easily be determined by those skilled in the art.

Additionally, the pharmaceutical composition may be administered orally or parenterally (e.g., intravenously, subcutaneously, intraperitoneally, or topically applied) according to the desired method. The administration dose depends on the patient's conditions and body weight, severity of disease, drug forms, and the route and time of administration, but it may be appropriately selected by those skilled in the art.

In a specific embodiment, the pharmaceutical composition may generally be administered in an amount of 0.001 mg/kg to 1,000 mg/kg, more specifically 0.05 mg/kg to 200 mg/kg, and most specifically 0.1 mg/kg to 100 mg/kg, once or in several divided doses daily, and a preferred dose may be appropriately selected by those skilled in the art according to the conditions and weight of a subject, severity of disease, drug forms, the route and duration of administration.

Still another aspect of the present invention provides a food composition for prevention or improvement of glioblastoma multiforme (GBM), which contains an extract of at least any one selected from the group consisting of *Platycodon grandiflorum, Scutellaria baicalensis, Phellodendron amurense* Ruprecht, and *Rubus coreanus*, or a fraction thereof as an active ingredient.

The terms used herein are as described above.

As used herein, the term "improvement" refers to all actions that at least reduce the level of parameters associated with the conditions being treated with the administration of the composition (e.g., severity of symptoms).

Since the extract of at least any one selected from the group consisting of *Platycodon grandiflorum, Scutellaria baicalensis, Phellodendron amurense* Ruprecht, and *Rubus coreanus* according to the present invention or a fraction thereof exhibits an excellent effect for the inhibition of glioblastoma multiforme (GBM), the extract or a fraction thereof may be contained in a food composition for the purpose of prevention or improvement of GBM. Since it is possible to take the food composition on a daily basis, a high effect can be expected for the prevention or improvement of GBM.

As used herein, the term "food" includes all of the foods in the ordinary sense, such as meat, sausage, bread, chocolate, candy, snacks, confectionery, pizza, ramen, other noodles, gum, dairy products (e.g., ice cream), various kinds of soups, beverages, teas, drinks, alcoholic beverages, vitamin complexes, health functional foods, etc., and the food is not limited thereto as long as it includes an extract of at least any one selected from the group consisting of *Platycodon grandiflorum, Scutellaria baicalensis, Phellodendron amurense* Ruprecht, and *Rubus coreanus* of the present invention or a fraction thereof.

As used herein, the term "health functional foods" means foods manufactured and processed using functional raw materials or ingredients beneficial for the human body according to the Health Functional Food Act No. 6727 of Korea, and the term "functionality" means controlling nutrients for the structure or functions of the human body or providing beneficial effects to health purposes, such as physiological effects, etc. Meanwhile, "health foods" means foods having an effect of active health maintenance or enhancement compared to general foods, and "health supplement foods" means foods for the purpose of supplementing health, and these terms of "health functional foods", "health foods", and "health supplement foods" may be used interchangeably in some cases.

The extract of at least any one selected from the group consisting of *Platycodon grandiflorum, Scutellaria baicalensis, Phellodendron amurense* Ruprecht, and *Rubus coreanus* according to the present invention or a fraction thereof may be added as it is or used with other foods or food ingredients, and may be appropriately used according to a conventional method.

The foods of the present invention may be manufactured by a method commonly used in the art, and in the case of the above manufacture, the foods may be prepared by adding raw materials and ingredients conventionally added in the art. Specifically, the food composition may further contain a physiologically acceptable carrier, and the type of carrier is not particularly limited, but any carrier commonly used in the art may be used. Additionally, the food composition may contain food additives, such as preservatives, bactericides, antioxidants, color fixing agents, coloring agents, bleaching agents, seasonings, sweeteners, flavoring agents, swelling agents, reinforcing agents, emulsifiers, thickeners, coating agents, gum base agents, antifoaming agents, solvents, improvers, etc. The additive may be selected according to the type of food and used in an appropriate amount.

Additionally, the food may be manufactured in any type of formulation without limitation as long as it is a formulation recognized as food. The food composition of the present invention has advantages in that it can be manufactured in various types of formulations, and due to the use of herbal medicine materials as raw materials unlike general medicines, it has no side effects, etc. that may occur during long-term use of medicines and provides excellent portability, and thus, it is possible to take the food composition of the present invention as a supplement so as to enhance the effect of preventing or improving glioblastoma multiforme (GBM).

In case where an extract of at least any one selected from the group consisting of *Platycodon grandiflorum, Scutellaria baicalensis, Phellodendron amurense* Ruprecht, and *Rubus coreanus* of the present invention or a fraction thereof exhibits an excellent effect of preventing or improving GBM, the extract or a fraction thereof may be contained in a food composition in various wt %. Specifically, the extract or a fraction thereof may be contained in an amount of 0.00001 wt % to 100 wt % or 0.01 wt % to 80 wt % relative to the total weight of the food composition, but the amount is not limited thereto. In case where the food composition is taken for a long period of time for health and hygiene purposes, the content may be below the above range, and since there is no problem in terms of safety, the active ingredients may also be used in an amount beyond the above range.

Still another aspect of the present invention provides a feed composition for prevention or improvement of GBM, which contains an extract of at least any one selected from the group consisting of *Platycodon grandiflorum, Scutellaria baicalensis, Phellodendron amurense* Ruprecht, and *Rubus coreanus* or a fraction thereof as an active ingredient.

The terms used herein are as described above.

Since an extract of at least any one selected from the group consisting of *Platycodon grandiflorum, Scutellaria baicalensis, Phellodendron amurense* Ruprecht, and *Rubus coreanus* according to the present invention or a fraction thereof exhibits an excellent effect for the treatment of glioblastoma multiforme (GBM), the extract or a fraction thereof may be contained in a feed composition for the purpose of prevention or improvement of GBM. Since it is possible for an animal to take the feed composition on a daily basis, a high effect can be expected for the prevention or improvement of GBM.

As used herein, the term "feed" refers to any natural or artificial diet, one meal diet, etc., or a component of the one meal diet for an animal to eat, ingest, and digest or those which are suitable for the same.

The type of feed is not particularly limited as long as the feed contains an extract of at least any one selected from the group consisting of *Platycodon grandiflorum, Scutellaria baicalensis, Phellodendron amurense* Ruprecht, and *Rubus coreanus* according to the present invention or a fraction thereof, and any feed commonly used in the art may be used. Non-limiting examples of the feed commonly used in the art may include vegetable feeds (e.g., grains, roots and fruits, food processing by-products, algae, fibers, pharmaceutical by-products, fats and oils, starches, gourds, grain by-products, etc.); and animal feeds (e.g., proteins, inorganics, fats and oils, minerals, fats and oils, single-cell proteins, animal plankton, foods, etc.). These feeds may be used alone or in combination of two or more kinds thereof, but are not limited thereto.

DETAILED DESCRIPTION OF THE INVENTION

Hereinafter, the present invention will be described in more detail with reference to the following Examples. However, these Examples are for illustrative purposes only and the scope of the invention is not limited by these Examples.

Inhibitory Effect of *Platycodon grandiflorum* Extract and Platycodin D Contained Therein Against Glioblastoma Multiforme (GBM)

EXAMPLE 1

Reagent

The extract of *Platycodon grandiflorum* provided by Hanpoong pharmaceutical company (Jeonju, Korea) as a dried powder was dissolved in distilled water. Platycodin D (PD) and U18666a were purchased from Cayman Chemical Company (Ann Arbor, Mich., USA). Bafilomycin A1, Rapamycin, z-vad-FAK, and methyl-beta-cyclodextrin were purchased from Sigma-Aldrich Co. (St. Louis, Mo., USA).

EXAMPLE 2

Cell Culture

The human glioma cell lines, U87MG and U373MG, were cultured respectively in RPMI-1640 (Welgene) and DMEM (Welgene, Daegu, Korea) supplemented with 10% fetal bovine serum (FBS, JR Scientific) and 1% antibiotics (Ab, Welgene). All cultures were maintained at 37° C. in a humidified incubator containing 5% $CO_2$.

EXAMPLE 3

Cell Viability Assay

Cell cytotoxicity was assessed by WST1 assay. U87 and U373 cells were each seeded in a 96-well plate ($5 \times 10^3$ cells/well) and treated with different concentrations of platycodin D (PD). Then, cells were incubated with a WST1 reagent (Dogen, Seoul, Korea) for 2 hours before reading the plate. Absorbance was measured at 450 nm using an ELISA reader (Versa Max, Molecular Devices, Sunnyvale, Calif., USA).

EXAMPLE 4

Protein Extraction and Immunoblot Analysis

Cells treated with the concentrations and materials described in FIGS. 1-3B, 7, 8, 10, 13, 16, 18, and 20 were lysed in buffer containing 20 mM Tris-HCl (pH 7.5), 150 mM NaCl, 1 mM EDTA, 1 mM $Na_2EDTA$, 1 mM EGTA, 1% NP-40, 1% sodium deoxycholate, 1 mM $Na_3VO_4$, 1 mM MPI, 1 mM PMSF, and PI cocktails for 15 to 20 minutes on ice. Cell lysates were separated by SDS-PAGE and transferred to nitrocellulose membranes. Immunodetection was performed with the following primary antibodies: rabbit anti-LC3B, rabbit anti-cathepsin B, rabbit-anti GAPDH (Cell Signaling Technology, Danvers, Mass.), mouse anti-SQSTM1/p62, and goat anti-cathepsin D (Santa CruzKPL, Gaithersburg, Md., USA) were incubated at room temperature for 1 hour. The protein bands were detected with ECL western Blotting Substrate (Thermo Fisher Scientific, Waltham, Mass., USA).

EXAMPLE 5

Reverse Transcription-Polymerase Chain Reaction (RT-PCR) Analysis

Total RNA was isolated using the Easy-Blue RNA extraction kit (iNtRON Biotech, Sungnam, Korea) according to the manufacturer's directions. 1 µg of the total RNA was reverse transcribed using a cDNA synthesis kit (TaKaRa, Otsu, Shinga, Japan) according to the manufacturer's instructions. The obtained cDNA was then amplified by PCR in a reaction mixture consisting of 10× Taq buffer, 2.5 mM dNTP mixture, Taq DNA polymerase (Takara), and corresponding primer sets. The primer sequences were as follows. Human SQSTM1-forward: 5'-GAA CTC CAG TCC CTA CAG ATG CC-3' (SEQ ID NO: 1), SQSTM1-reverse: 5'-CGG GAG ATG TGG GTA CAA GG 2-3' (SEQ ID NO: 2); Human LDLR-forward: 5'-CAG ATA TCA TCA ACG AAG C-3' (SEQ ID NO: 3), LDLR-reverse: 5'-CCT CTC ACA CCA GTT CAC TCC-3' (SEQ ID NO: 4); Human GAPDH-forward: 5'-CGT CTT CAC CAC CAT GGA GA-3' (SEQ ID NO: 5), GAPDH—reverse: 5'-CGG CCA TCA CGC CAC AGT TT-3' (SEQ ID NO: 6). The PCR products were analyzed by 1.5% agarose gels.

EXAMPLE 6

GFP-LC3B Assay

Cultured cells seeded in plates with microscope coverslips were transfected with a pGFP-LC3B plasmid using Lipofectamine 3000 (Thermo Fisher Scientific) according to the manufacturer's instructions. After the transfection, the cells were fixed with 4% paraformaldehyde (PFA) in phosphate-buffered saline (PBS) at room temperature for 10 minutes. The images were examined under a laser confocal microscope (Zeiss, Oberkochen, Baden-Wurttemberg, Germany). At least 50 to 100 cells/sample were counted per experiment and representative results are shown in FIGS. 4, 5, 11, 12 and 18C.

EXAMPLE 7

Immunofluorescence Analysis

Cells treated with the materials were permeabilized with 0.01% Triton X-100 in PBS. After blocking the resulting cells in 2% bovine serum albumin (BSA) in PBS, they were incubated at 4° C. with a primary antibody against SQSTM1/p62 (Santa Cruz) overnight. The stained cells were incubated with an Alexa594-conjugated secondary antibody (Invitrogen, Calif., USA). The images were examined under a Zeiss laser confocal microscope.

EXAMPLE 8

Lysotracker Assay

To stain acidic compartments, 50 nM LysoTrackerRedDND-99 (Thermo Fisher Scientific) was added to a medium at 37° C. with 5% $CO_2$ for 30 minutes prior to fixation. The nuclei were labeled with 4,6-diamidino-2-phenylindole (DAPI, Sigma). The slides were finally mounted using a Faramount mounting medium (Dako, Glostrup, Denmark). The images were examined under a Zeiss laser confocal microscope.

EXAMPLE 9

DQ Red-BSA Trafficking Assay

Cells were placed on coverslips prior to treatment with the materials and continuously loaded with DQ Red-BSA (Invitrogen) at a working concentration of 10 µg/mL in a culture medium at 37° C. for 30 minutes. The cells were fixed in 4% PFA and then subjected to DAPI staining. The images were examined under a Zeiss laser confocal microscope. The number of DQ Red-BSA spots was quantified using ImageJ software.

EXAMPLE 10

Cholesterol Cell-Based Detection Assay

Cells grown on coverslips were treated with the materials. Then, the cells were fixed with 4% PFA at room temperature for 10 minutes. The solution of Filipin III (Cayman) was added for staining of parenteral cholesterol and the samples were incubated in a dark room for 30 minutes. The images were examined under a Zeiss laser confocal microscope.

EXAMPLE 11

Cholesterol Measurement

Cells treated as described above were processed using a total cholesterol assay kit (STA384, Cell Biolabs) according to the manufaterer's instructions. Cholesterol esters and free cholesterol were quantified by homogenizing $10^6$ cells extracted from a 200 µL mixture of chloroform: isopropanol: NP-40 (7:11:0.1). After centrifugation of the extract at 15,000× g for 10 minutes, the organic phase was collected and evaporated at 50° C. The extract was resuspended in 200 µL of a 1× cholesterol assay diluent prior to analysis. The colorimetric signal was analyzed using an ELISA reader (Versa Max, Molecular Devices, Sunnyvale, Calif., USA) at 540 nm. Cellular cholesterol results were reported as µg of cholesterol per mg of cell protein.

EXAMPLE 12

Cell Surface LDLR Analysis

Cells treated as described in FIG. 16 were separated from plates and resuspended in PBS. After washing with 1% BSA in PBS, the cells were incubated with a primary antibody against human LDLR (Abcam) for 30 minutes. Then, the cells were washed before incubation with an Alexa-Fluor 488-conjugated secondary antibody (Invitrogen) for 30 minutes. The stained cells were washed and resuspended. Fluorescence was analyzed by a FACScalibur flow cytometer (Becton Dickinson, San Jose, Calif., USA) using CellQuest™ software.

EXAMPLE 13

LDLR Uptake Assay

Cells seeded on coverslips were treated with the materials and then the culture medium was replaced with BODIPY™ FL LDL (Thermo Fisher Scientific) at a working concentration of 5 µg/mL in a medium. The cells were additionally incubated at 37° C. for 1 hour. The degree of LDL uptake was measured using a Zeiss laser confocal microscope.

EXAMPLE 14

Preparation of shRNA shRNA sequences against LDLR were cloned into a lentiviral vector. For the production of lentivirus, the vectors were co-transfected with psPAX2 and pMD2.G in 293T cells using Lipofectamine 3,000 (Invitrogen). Then, the cultured medium was harvested. The viral supernatant was applied to GBMs and cells were selected in puromycin for 3 additional days. The shRNA sequence was as follows.
shLDLR sequence: 5'-CCACTTGTAGGAGATGCAT-3' (SEQ ID NO: 7).

EXAMPLE 15

Clonogenic Assay

Approximately $2 \times 10^3$ cells were seeded into each 6-well plate and then treated as described in FIG. 19. After 7 days, the cells were washed with PBS and stained with 0.5% crystal violet.

Experimental Result 1. Screening of Herbal Medicines for Finding Novel Autophagy Inhibitors To discover novel autophagy inhibitors, 26 herbal medicines were screened by western blot analysis. During autophagy, LC3 (microtubule-associated protein light chain 3) protein recruited from the cytosol (LC3-I) to phosphatidylethanolamine (PE)-containing autophagosomal membrane, forming a lipidated form of LC3 (LC3-II). The LC3-II is currently most widely used as an autophagosome marker because its level correlates with the number of autophagosomes. The effects of herbal medicines on expression of LC3-II levels were examined in glioblastoma (GBM) including U87MG and U373MG cells. As can be confirmed in FIG. 1, the western blot analysis showed that several herbal medicines including *Rubus coreanus, Forsythia suspense*, and *Poncirus trifoliata* increased LC3B-II levels in U87MG cells, but only *Platycodon grandiflorum* (PG) was effective in U373MG cells. An alternative marker for assessing the autophagic flux is p62/SQSTM1, a protein that is selectively degraded during clearance of aggregated proteins in autophagosomes. Therefore, the effect of each herbal medicine on the change in the p62 level was evaluated, given that a rise in the amount of p62 is related to the inhibition of autophaic flux. Notably, as can be confirmed in FIG. 1, only PG increased the p62 level in both cell lines among all the tested herbal medicines. Based on these results, PG was selected to examine its effects on autophagy in GBM cells.

Experimental Result 2. *Platycodon randiflorum* extract displays anti-autophagic effects.

To confirm the PG effects on autophagy in GBM cells, U87MG and U373MG cells were treated with various concentrations of PG in a range of 50 μg/mL to 1,000 μg/mL for 24 hours and examined the levels of LC3-II and p62 by western blot analysis. As can be confirmed in FIG. 2A, it was confirmed that the LC3B-II level was increased in a dose-dependent manner with the maximum activity at 500 μg/mL of PG. In addition, the upregulation of LC3B-II reached a maximum at 24 hours after treatment of 500 μg/mL of PG in both cells. The dose dependence and time kinetics of the p62 expression after PG treatment displayed similar results with the LC3-II western blot data. These data implicate that the extracts of PG contain an effective inhibitor for blocking autophagy.

Experimental Result 3. PD is Active Compound from Extract of PG to Impair Autophagic Flux.

To identify active compounds from the extracts of PG for inhibiting autophagy, platycodin D (PD), which is a main saponin isolated from PG, was selected. U87MG and U373MG cells were treated with varying concentrations of PD for 24 hours and examined the changes in the LC3 and p62 levels. As can be confirmed in FIG. 3A, western blot analysis showed dose-dependent increases in the LC3B-II and p62 levels and maximum activity at 10 μM PD. As can be confirmed in FIG. 3B, time-dependent increases in the LC3B-II and p62 levels were also observed in GBM cells treated with 10 μM PD. In order to determine whether the PD-induced p62 accumulation is due to the transcriptional activation of p62, an RT-PCR was performed to assess p62 mRNA levels in the presence or absence of PD. As can be confirmed in FIG. 3C, PD treatment did not alter the p62 mRNA levels in both GBM cells, suggesting that the increase in the p62 level by PD treatment is caused by blockade of p62 degradation rather than transcriptional induction of p62. Overall, these data demonstrate that PD is an active compound in PG for suppressing autophagy.

Experimental Result 4. PD Induces Accumulation of GFP-LC3B puncta.

To confirm the western blot data, the LC3B accumulation in GBM cells was monitored using a confocal microscope. Both U87MG and U373MG cells transfected with a green fluorescent protein (GFP)-tagged LC3 expression plasmid were treated with 10 μM PD for 24 hours and examined under a confocal microscope. As can be confirmed in FIG. 4, while green fluorescence was visualized as a diffuse staining in control cells, PD treatment markedly increased the formation of GFP-LC3B puncta in both cells. Quantification of GFP-LC3 puncta per cell with Image J software showed a 10.1-fold increase (3.76±0.66 in DMSO vs. 38.03±5.75 in PD) and a 8.9-fold increase (3.68±1.45 in DMSO vs. 32.84±3.98 in PD) in U87MG and U373 cells, respectively. These results indicate that PD is very effective in increasing autophagosome formation in GBM cells.

Experimental Result 5. PD accumulates p62 in autophagosomes. Since p62 localizes in autophagosomes via binding to LC3 and serves as an adaptor protein in degradation of ubiquitinated proteins, the inhibition of autophagy blocks degradation of p62 and ubiquitinated proteins, leading to p62 accumulation. Based on the earlier observations that PD increases the p62 level in western blotting, the effects of PD on p62 through immunofluorescence analysis were confirmed. U87MG and U373MG cells transfected with GFP-LC3 were treated with 10 μM PD for 24 hours and processed with anti-p62 antibodies. As can be confirmed in FIG. 5, PD treatment led to an increase in both cells in p62 staining and colocalization with GFP-LC3B puncta. Similar results were obtained when the cells were treated with Bafilomycin A1 (BafA1), which is a well-known autophagy inhibitor. These data support the notion that PD inhibits autophagy at a late stage by blocking autophagic degradation.

Experimental Result 6. PD Promotes Reduction in Cell Viability and Vacuole Formation in GBM.

Figure 6A:
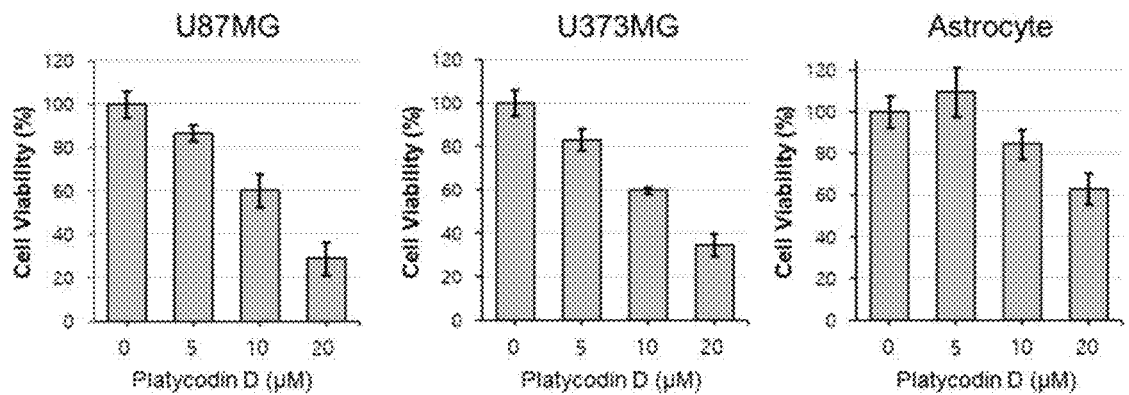
FIGS. 6A and 6B show the results that PD induces a decrease in cell viability and vacuole formation.
Figure 6B:
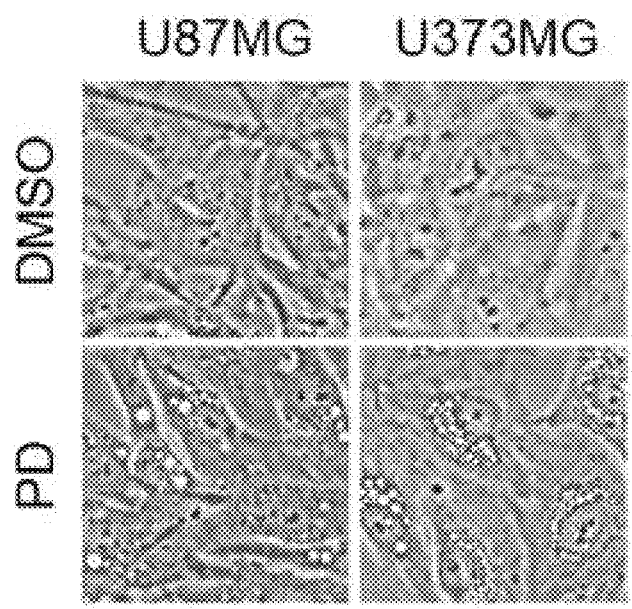
Figure 7A:
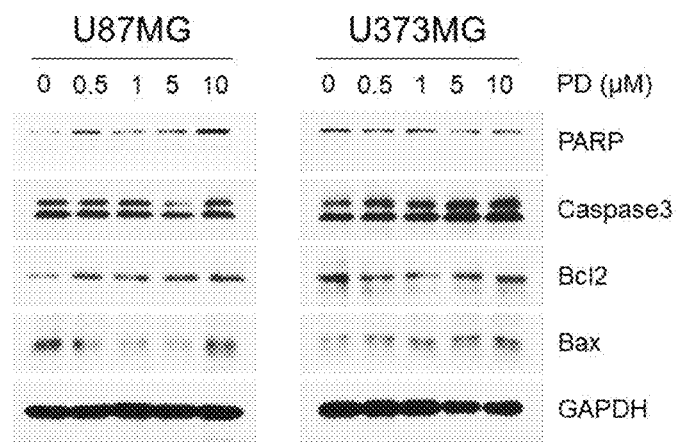
FIGS. 7A and 7B show the results that PD induces non-apoptotic cell death.
Figure 7B:
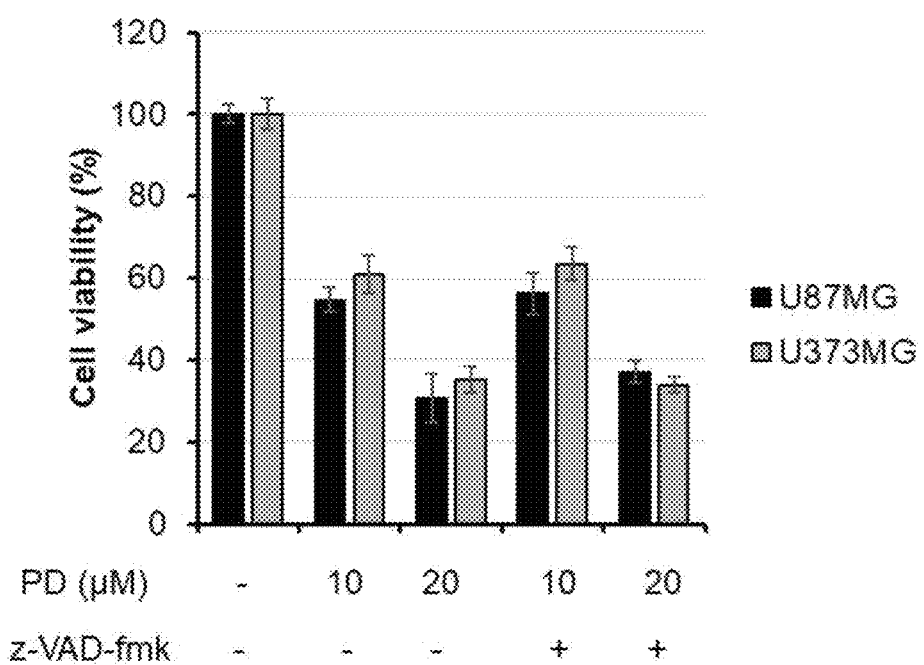
Figure 8:
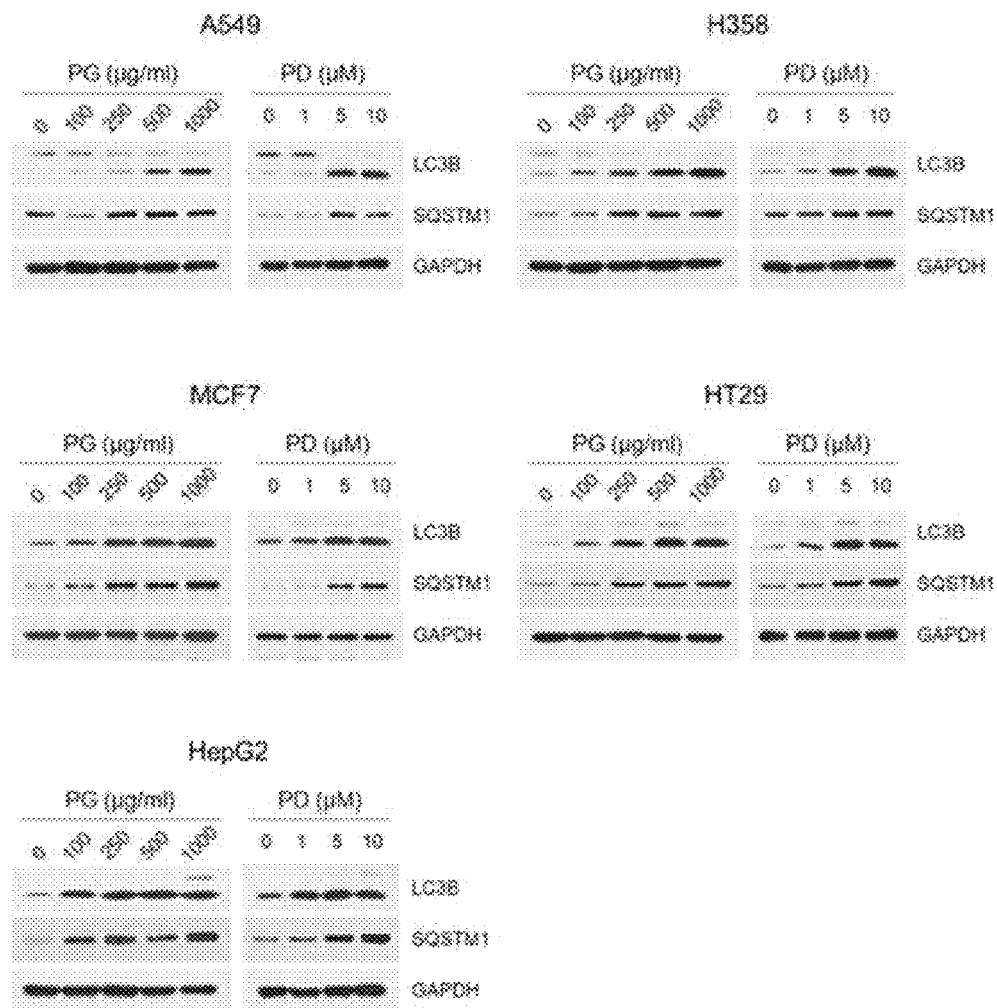
FIG. 8 shows the results that the extracts of PG and PD exhibit defects in autophagic activities in various cancer cell lines. After treatment with indicated concentrations of PD or PG for 24 hours, the protein levels of LC3B and SQSTM1 were detected by immunoblot analysis in several cancer cell lines including A549 and H358 (lung cancer), MCF7 (breast cancer), HT29 (colon cancer), and HepG2 (liver cancer). GAPDH was used as a loading control.

Inhibition of autophagy has been reported to cause cancer cell death. Therefore, the cytotoxic effects of PD on U87MG, U373MG, and normal astrocytes were examined. After treating these cells with various doses of PD for 48 hours, their cell viability was analyzed by WST1 assays. As can be confirmed in FIG. 6A, the percentage of viable cells was significantly decreased in the PD-treated GBM cells in a dose-dependent manner. Notably, the PD treatment at 10 µM, which is a concentration for effective inhibition of autophagy, resulted in approximately 60% of cell viability in GBM cells. Importantly, the PD-mediated reduction in cell viability was less effective in normal human astrocytes, indicating that PD could target only GBM cells in a specific manner. As can be confirmed in FIG. 6B, morphological changes were also visualized by an optical microscope after exposure of GBM cells to 10 µM PD for 24 hours. Both cells exhibited cytoplasmic vacuoles which would be observed in cells undergoing autophagy. Taken together, these findings suggest that PD decreases cell viability in GBM cells in a cancer cell-specific manner and this might be related to the cytoplasmic vacuolization.

Experimental Result 7. PD Does Not Induce Apoptotic Cell Death in GBM Cells.

Numerous studies have suggested that impairment of autophagy leads to a reduction in recycling cellular constituents for energy production and consequently contribute to apoptotic cell death. Therefore, whether PD-mediated autophagy inhibition promotes apoptosis in GBM cells was examined by western blot analysis. Activation of caspase-3 and cleavage of its substrate, PARP, are hallmarks of apoptosis. Upon treatment of U87MG and U373MG cells with PD, there was no significant induction of caspase-3 activation and PARP cleavage. In addition, as can be confirmed in FIG. 7A, the expressions of Bcl2 and BAX, which are apoptosis regulators, were not changed in response to PD treatment. Finally, the effects of z-VAD-fmk, which is a broad spectrum caspase-inhibitor, on PD-induced cell death were examined by WST1 assay. As can be confirmed in FIG. 7B, co-treatment of PD and z-VAD-fmk had little impact on the cell viability, compared to PD-alone treatment in both GBM cells. Together, these data strongly suggest that apoptosis is not involved in PD-mediated GBM cell death.

Experimental Result 8. PG and PD Show Anti-Autophagic Activities in Multiple Types of Cancer.

Recently, PD has been suggested as an inducer for autophagy-dependent cell death in many cancers, such as lung and hepatocellular carcinoma. In these studies, they were carried out to examine the accumulation of LC3B-II without checking p62 levels upon PD treatment and conclusions were drawn that PD acts as an inducer of autophagic cell death in these cancer cells. In order to clarify the role of PD in autophagic flux, whether PD increases the p62 level, as observed in GBM cells, was examined in different types of cancer cells including A549, H358, MCF7, HT29 and HepG2. As can be confirmed in FIG. 8, the enhanced level of p62 together with LC3-II was observed upon treatment of PG and PD in all cancer cells tested in a dose-dependent manner, providing the evidence that PG and PD could be universal autophagy inhibitors.

Experimental Result 9. PG and PD Show Anti-Autophagic Activities in Multiple Types of Cancer.

Figure 9A:
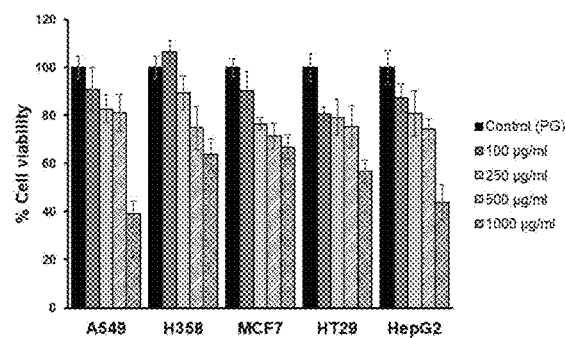
FIGS. 9A to 9C show the results that PD decreases cell viability and vacuole formation in various cancer cell lines.
Figure 9B:
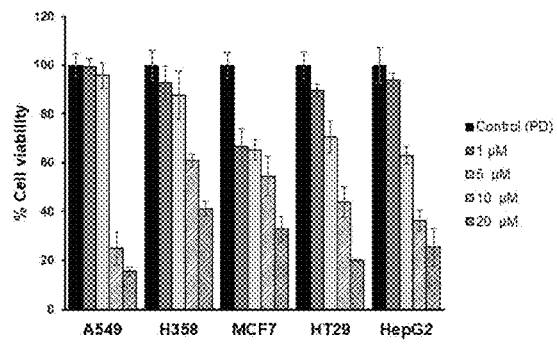
Figure 9C:
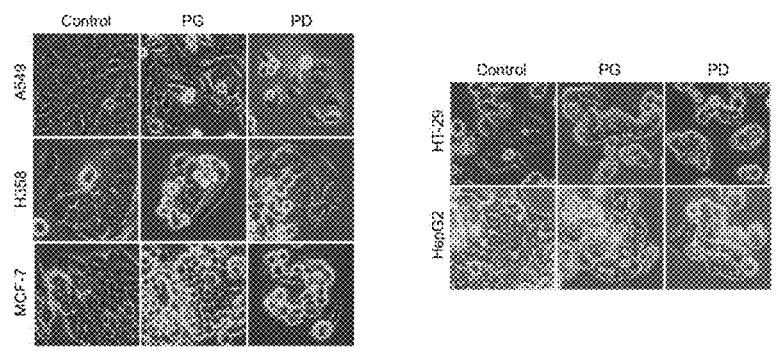
Figure 10A:
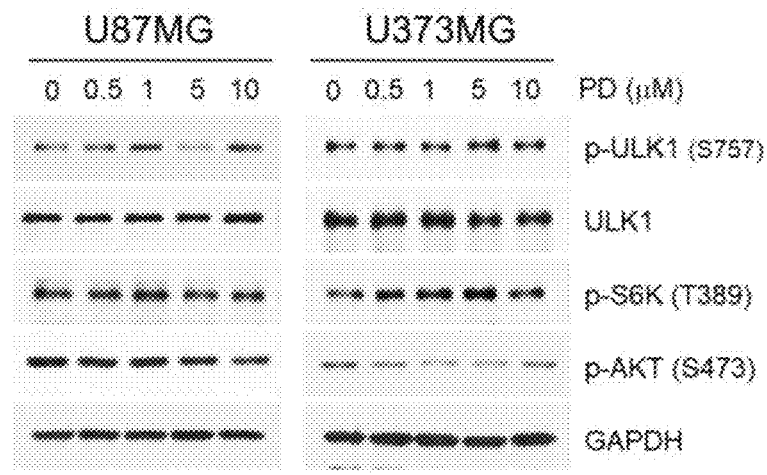
FIGS. 10A to 10D show the results that PD-mediated autophagy inhibition is independent of mTOR and MAPK signaling pathways.
Figure 10B:
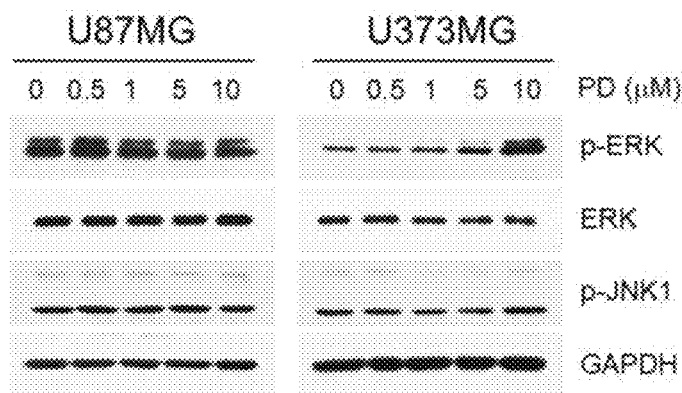
Figure 10C:
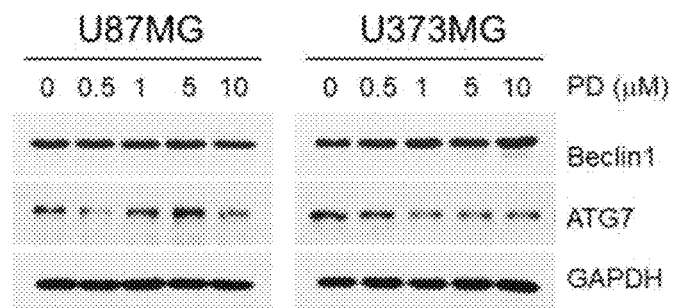
Figure 10D:
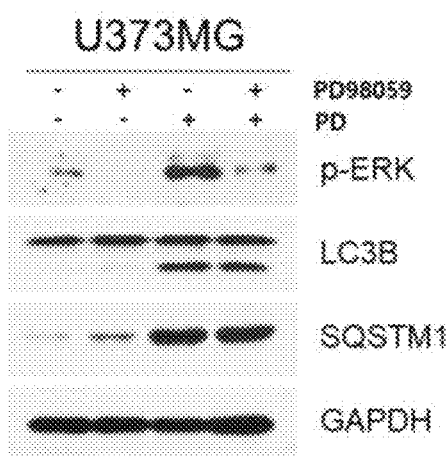
Figure 11:
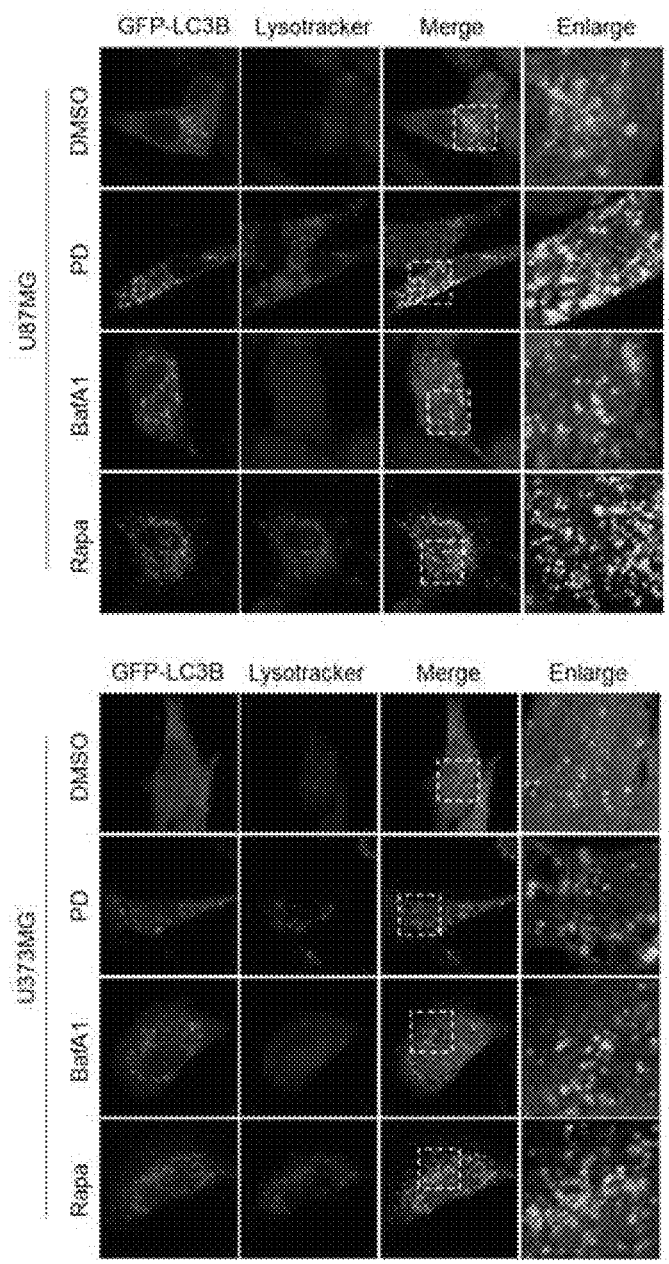
FIG. 11 shows the results that PD blocks the fusion of autophagosomes with lysososmes. Cells transiently expressing GFP-LC3B (green) were exposed to PD (10 μM), BafA1 (100 nM), and Rapa (1 μM) for 24 hours. Then, cells were stained with LysoTracker (red) and DAPI (blue). The merged images show an overlap between GFP-LC3 and LysoTracker (yellow). The panels on the right are higher-magnification images of the boxed regions.
Figure 12:
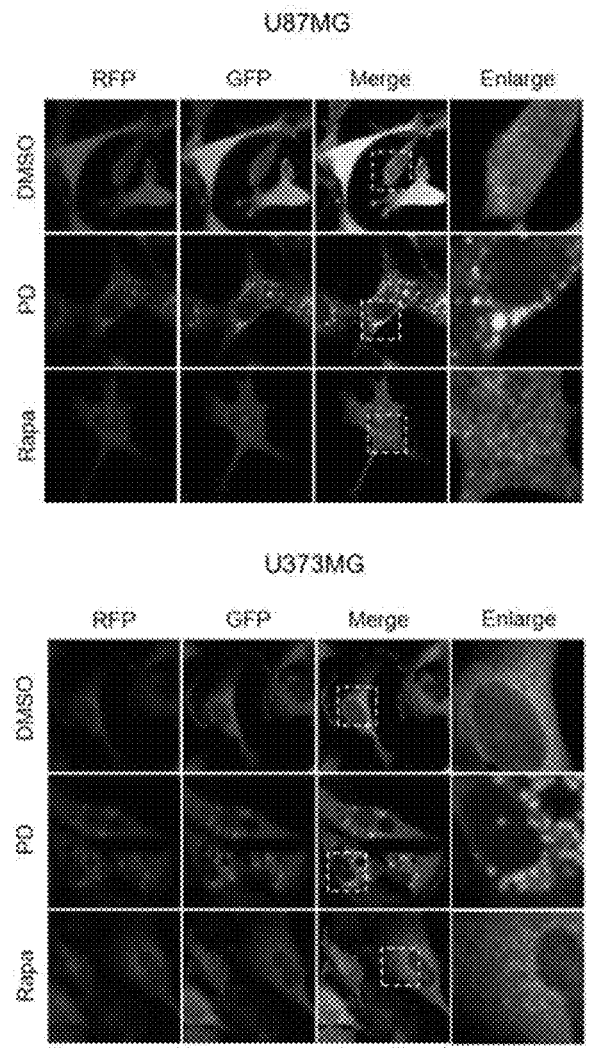
FIG. 12 shows the results that PD inhibits autolysosome formation in GBM cells. Cells stably expressing mRFP-GFP-LC3 were incubated with PD (10 μM) or Rapa (1 μM) for 24 hours, and then analyzed by confocal microscopy. The merged images (yellow) show an overlap between GFP-LC3 (green) and mRFP-LC3 (red). The panels on the right are higher-magnification images of the boxed regions.
Figure 13:
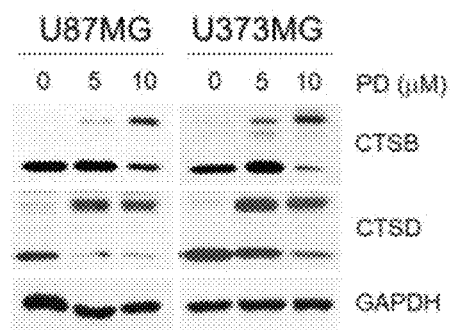
FIG. 13 shows the results that PD inhibits the activities of cathepsin B and D. Cells were treated with PD (5 μM and 10 μM) for 48 hours. Immunoblot analyses for the processing of endogenous CTSB and CTSD are shown (upper, immature form/lower, mature form of CTSB and CTSD). GAPDH was used as a loading control.

Previously, PD was reported to inhibit cell viability in various cancer cell lines. To further confirm the effects of PD on the cytotoxicity of cancer cells, WST1 assay was performed following treatment with different concentrations of PD. In accordance with the earlier reports, as can be confirmed in FIG. 9B, PD suppressed the viability in a dose-dependent manner in all cell lines tested. In addition, as can be confirmed in FIG. 9A, treatment with PG also resulted in a marked decrease in the viability of these cells. To examine whether PG also develops vacuoles in other cancer cells, as can be confirmed in FIG. 9C, visible vacuoles were observed in all PD and PG-treated cells using an optical microscope. These results were in accordance with previous reports suggesting that PD exhibited an antitumor activity.

Experimental Result 10. PD-Mediated Autophagy Inhibition is Independent of mTOR and MAPK Signaling Pathway.

Previous studies have shown that PD enhances autophagy via mTOR/MAPK pathway. In order to analyze the molecular mechanisms of PD-mediated autophagy in GBM cells, several regulatory components for autophagy were examined by immunoblot analysis. It is known that mTORC1 activation, measured by S6K phosphorylation, inhibits autophagy initiation by phosphorylating the ULK1 (Ser 757). The results showed that there is no alteration in the phosphorylation of S6K and ULK1 in PD-treated GBM cells. Furthermore, as can be confirmed in FIG. 10A, altered phosphorylation of AKT, which is a positive regulator of mTORC1, was not observed in these cells. The effects of PD on MAPK pathway in GBM cells were also examined because previous studies indicated that PD induced autophagy by the activation of MAPK including ERK and JNK in several types of cancer cell lines. As can be confirmed in FIG. 10B, there was no significant difference in phosphorylation levels of JNK between control cells and PD-treated cells. Interestingly, the phosphorylation levels of ERK were markedly increased upon PD treatment in U373MG, but not in U87MG. In order to assess a role of the ERK phosphorylation in autophagy regulation in PD-treated U373MG cells, PD98059, which is a inhibitor of MEK (i.e., an upstream activator of ERK), was added before PD treatment and the changes in LC3-II and p62 levels were examined by western blotting. As can be confirmed in FIG. 10D, PD98095 treatment effectively inhibited the phosphorylation of ERK, but it did not alter the levels of LC3B-II and p62 in U373MG cells, indicating that ERK activation shown in PD-treated U373MG cells is not related to autophagy regulation. Finally, key proteins for autophagosome assembly signals (e.g., Beclin-1 and ATG7) were observed in both cells. As can be confirmed in FIG. 10C, there were no significant changes in both protein levels. Collectively, these data suggest that PD has no effect on the upstream actions of autophagy in GBM cells, which is not consistent with the results observed in previous reports using other types of cancer cells.

Experimental Result 11. PD Blocks Fusion of Autophagosomes with Lysosomes. Since p62 was accumulated in autophagosomes by PD treatment, it was speculated that PD may cause the lysosomal dysfunction like bafilomycin A1, which inhibits vacuolar $H^+$-ATPase (V-ATPase)-dependent lysosomal acidification and blocks autophagosome-lysosome fusion. Thus, the PD-treated cells with LysoTracker Red, which is a marker for acidic compartment including lysosomes was stained to examine the colocalization of GFP-LC3B. As can be confirmed in FIG. 11, it was found that PD-treated cells exhibited a significant separation of GFP-LC3B and LysoTracker Red staining, similar to what is shown following BafA1 treatment. In contrast, this effect was inhibited in the presence of rapamycin, which induces autophagy including a fusion between autophagosomes and lysosomes. Notably, the LysoTracker Red fluorescence in PD-treated cells was similar to that of rapamycin-treated cells, while being in contrast to that of BafA1-treated cells, indicating that PD does not affect lysosomal acidification. These results indicate that PD inhibits the fusion of autophagosomes with lysosomes without affecting lysosomal acidity.

Experimental Result 12. PD Inhibits Autophagosome Maturation into Autolysosomes.

In order to examine whether PD induces accumulation of autophagosomes by inhibiting their maturation into autolysosomes, a tandem-tagged fluorescent reporter, mRFP-GFP-LC3, was used. The GFP fluorescence of the fusion protein is rapidly quenched in lysosomal acidic conditions, whereas the RFP fluorescence is relatively stable. The yellow dots in the merged image are indicative of autophagsomes and solely dots correspond to autolysosomes. The mRFP-GFP-LC3 plasmids were transfected into U87MG and U373MG cells, treated with PD for 24 hours, and subjected to confocal microscopy.

Treatment with an autophagy inducer, rapamycin, resulted in an increase in mRFP dots, and GFP signal was attenuated in the acidic conditions of autolysosome. However, as can be confirmed in FIG. 12, in PD-treated cells, GFP-positive dots were retained and colocalized with mRFP dots, forming yellow dots fluorescence in both GBM cells, suggesting a blockade of maturation into autolysosomes.

Experimental Result 13. PD Inhibits Lysosomal Protease Activity.

To confirm whether PD functions as an autophagy inhibitor, the effects of PD on lysosomal proteases, cathepsin B and D, were examined Autophagy is a lysosome-mediated and self-degradative process that requires lysosomal cysteine proteases known as cathepsins. Since pro-cathepsins are cleaved into a mature form in lysosomes, the 33 kD active cleaved form of cathepsins has been commonly used as a marker for lysosomal activity. As can be confirmed in FIG. 13, while the mature forms of cathepsin B and D proteins were decreased, immature forms of those protein were increased after PD treatment in U87MG and U373MG cells, implying that PD suppresses a lysosomal function by downregulating the lysosomal proteolytic activity.

Experimental Result 14. PD Impairs Lysosomal Proteolytic Activity.

To confirm the lysosomal activity in PD-treated GBM cells, the DQ-BSA assay was performed to assess lysosomal protein degradation. In DQ-BSA, which is a red BODIPY dye conjugated to bovine serum albumin (BSA), the BSA is so heavily conjugated that the red fluorescence is self-quenched. Upon cleavage of the DQ-BSA by proteolytic enzymes in lysosomal compartments, this quenching is relieved, generating red fluorescence. Thus, DQ-BSA is a useful tool to visualize a lysosomal proteolytic activity. As can be confirmed in FIG. 13, treatment of U87MG and U373MG cells with PD caused a significant reduction in red fluorescence compared to the cells reduced with DMSO. Similar results were obtained in BafA1-treated GBM cells. These data imply that PD impairs the lysosomsomal proteolytic activity in GBMs.

Experimental Result 15. PD Accumulates Cholesterol in Lysosomes.

Figure 14:
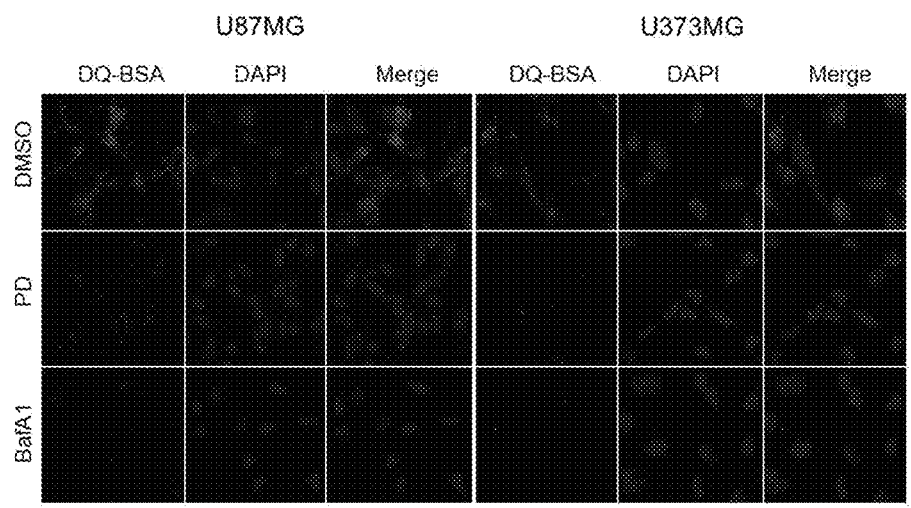
FIG. 14 shows the results that PD impairs proteolytic activity in lysosomes. Cells were incubated with DMSO, PD (10 μM), or BafA1 (100 μM) for 24 hours, and then the cells were treated with DQ-BSA (10 μM) for 30 minutes. Data shown are representative images of each sample. The fluorescence intensity of DQ-BSA was quantified with ImageJ software. More than 100 cells were counted in each condition and the number of puncta per cells is presented as means±SD from three independent experiments.
Figure 14:
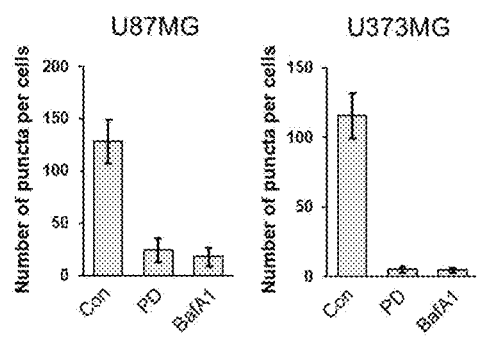
Figure 15A:
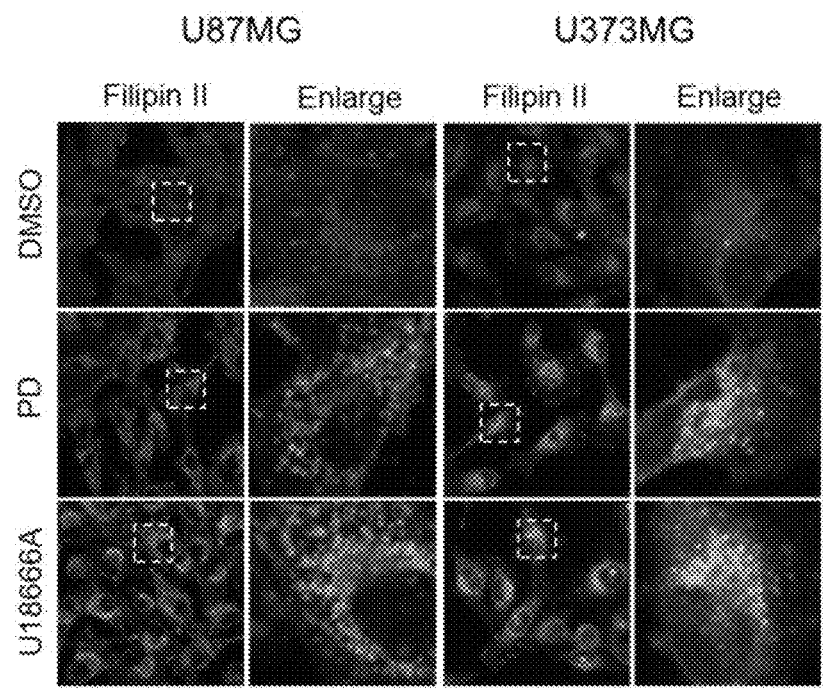
FIGS. 15A and 15B show the results that PD promotes accumulation of cholesterol in lysosomes. Cells were treated with DMSO, PD (10 μM), or U18666a (1 μM) for 24 hours.
Figure 15B:
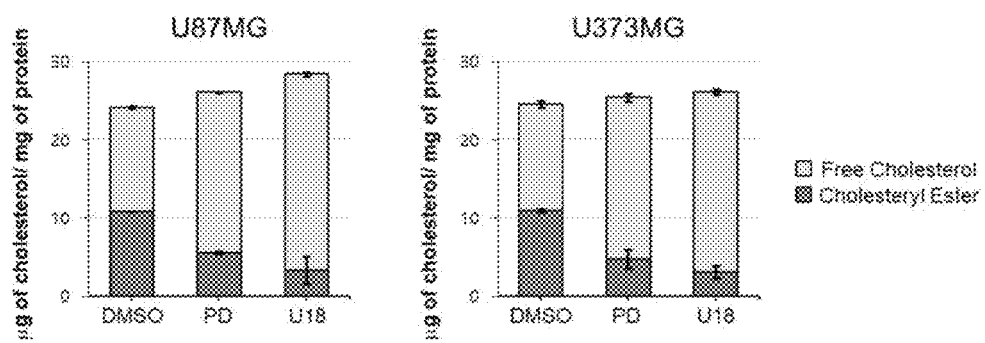
Figure 16A:
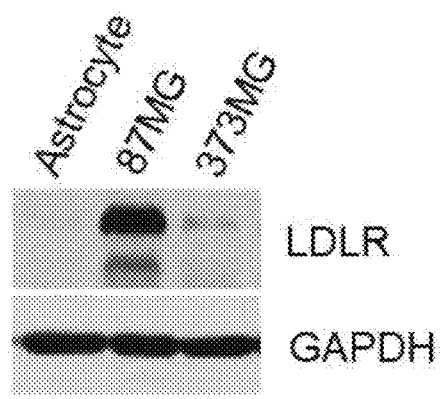
FIGS. 16A to 16D show the results that PD increases the expression of LDLR on cell surfaces in GBM cells.
Figure 16B:
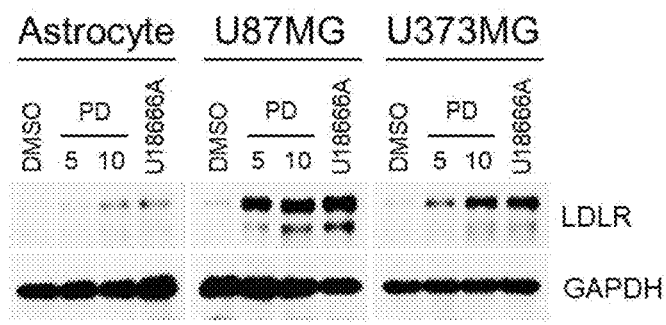
Figure 16C:
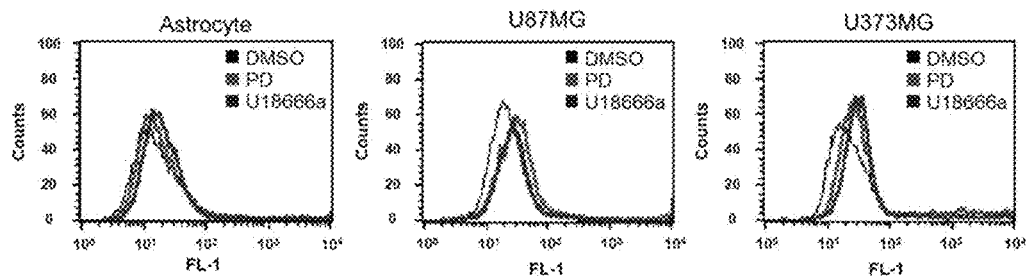
Figure 16D:
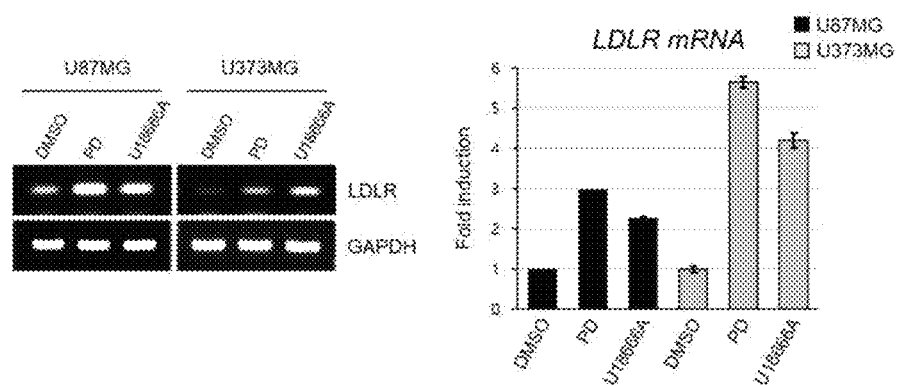

The present inventors concluded that PD inhibits the maturation of autophagosome into autolysosomes by inhibiting lysosomal degradation and an autophagosome-lysosome fusion in GBM cells. A few studies have suggested that intracellular cholesterol plays an important role in positioning of autophagosomes or lysosomes for a fusion between these compartments. To examine whether the defect in the autophagosome-lysosome fusion by PD is due to altered intracellular cholesterol levels, the PD-treated GBM cells were stained with filipin-III, which is a fluorescent dye that binds to cholesterol. Confocal imaging showed that PD induces cholesterol accumulation within intracellular vesicles. As can be confirmed in FIG. 14A, this filipin-III staining pattern is very similar to that found in GBM cells treated with U18666A, implying that PD blocks cholesterol release from lysosome and accumulates cholesterol in lysosomes. In addition, the assay with the total cholesterol measurement kit revealed a significant increase of free cholesterol levels in GBM cells after treatment with PD or U18666A. The filipin-III staining patterns between PD- and U18666A-treated GBM cells imply that PD accumulates cholesterol in intracellular vesicles and suggest that it may become a lysosome.

Experimental Result 16. PD Increases Cell Surface Expression of LDLR in GBM Cells.

Brain is the most cholesterol-rich organ of the body, containing about 20% of total body cholesterol. Previous studies demonstrated that GBM cells, unlike normal human astrocytes which primarily rely on endogenous cholesterol synthesis, depend on uptake of exogenous cholesterol for their survival, thereby increasing the expression of low-density lipoprotein receptors (LDLRs) on their cell surface. As can be confirmed in FIG. 16A, in consistent with these reports, the LDLR protein level was markedly elevated in U87MG and U373MG cells relative to normal human astrocytes. Upregulation of LDLR was observed in U18866A-treated cells through sequestration of free cholesterol in lysosomes. Therefore, it was found that PD can also increase the LDLR expression in GBM cells. In consistent with this hypothesis, PD significantly increased the LDLR expression in U87MG and U373MG cells as well as in normal astrocytes, but the degree of LDLR expression was more prominent in GBM cells than in normal astrocytes. In addition, as can be confirmed in FIG. 16B, as expected, U18666A increased the LDLR expression in all three types of cells, similar to that observed in PD-treated cells. Then, the cell surface expression of LDLR was confirmed by flow cytometry. GBM cells treated with PD or U18666A showed a similar pattern of shift of the FL-1 histogram peak toward right, indicating that the LDLR expression on cell surface was increased by PD or U18666A. However, as can be confirmed in FIG. 16C, the changes in peak shift were very negligible in the PD or U18666A-treated astrocytes, which were equivalent to the results obtained by western blot. Taken together, these data demonstrate that PD significantly increases the LDLR expression on the surface of GBM cells compared to normal astrocytes.

Experimental Result 17. PD Accelerates Uptake of Exogenous LDL in GBM Cells

Figure 17:
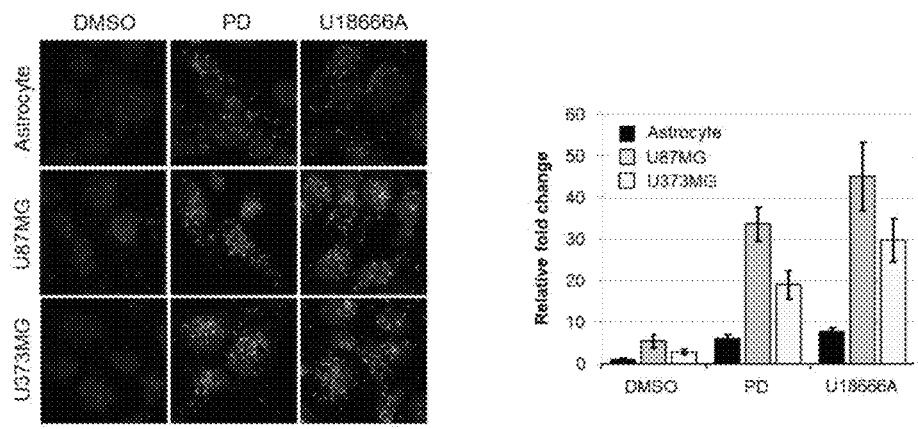
FIG. 17 shows the results that PD increases the uptake of exogenous LDL in GBM cells. Cells were treated with DMSO, PD (10 μM), or U18 (1 μM) for 24 hours and subsequently loaded with BODIPY™ FL LDL. BODIPY-LDL uptake was visualized by confocal microscopy. Nuclei were stained with DAPI (blue). Quantification shown on the right graph represents a relative fold change from three independent experiments±SD.

Based on the previous study results of the present inventors that PD increases cell surface LDLR expression and accumulate cholesterol within lysosomes, whether PD can increase the uptake of exogenous LDL was examined Cells pretreated with PD or U18666A were incubated with BODIPY FL-labeled LDL particles for 1 hour and the LDL uptake was observed by a confocal microscope. Upon analysis of these cells, it was observed that PD caused about a 6-fold increase in LDL uptake and it was a level similar to that detected in the U18666A-treated cells. Notably, as can be confirmed in FIG. 17, the LDL uptake was less effective in normal astrocytes treated with PD- or U18666A-. These results indicate that PD accelerates LDL uptake by the increased LDLR proteins on cell surface in GBM cells.

Experimental Result 18. Cholesterol Depletion Restores PD-Mediated Impairment of Autophagy Flux.

Figure 18A:
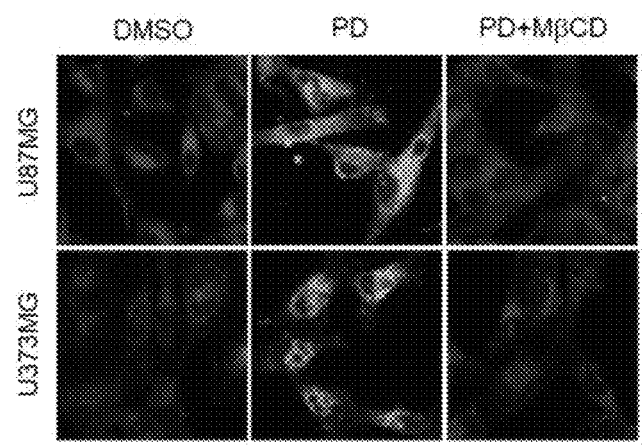
FIGS. 18A to 18C show the results that MβCD restores PD-mediated inhibition of autophagy flux and cathepsin B activity.
Figure 18B:
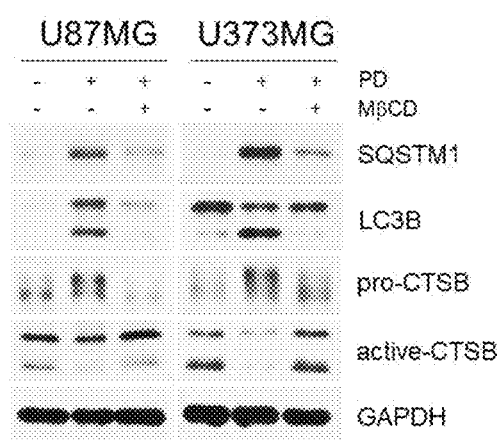
Figure 18C:
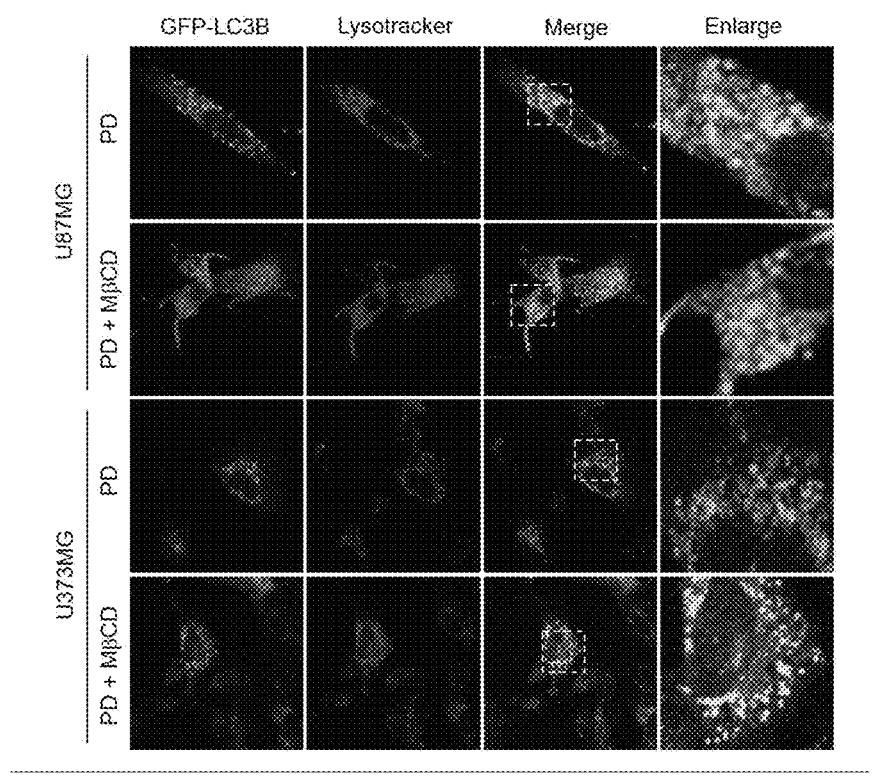

To examine the interplay between PD-mediated cholesterol accumulation in lysosomes and inhibition of autophagy, the cellular cholesterol in PD-treated GBM cells was depleted by methyl β-cyclodextrin (MβCD), which is a cholesterol-chelating agent, and their effects on autophagy were examined First, as can be confirmed in FIG. 18A, it was observed that the addition of MβCD into PD-treated GBM cells successfully depleted the accumulated cholesterol in lysosomes. In particular, as can be confirmed in FIG. 18B, the combined treatment with MβCD and PD almost completely restored the changes in the LC3-II and p62 levels which were increased by the treatment of PD alone in both GBM cells. Moreover, the recovered activity of cathepsin B was also detected by the addition of MβCD. Considering that MβCD restored autophagy flux and a lysosomal activity, it was speculated that MβCD could have an impact on the PD-mediated defective autophagosome-lysosome fusion. As expected, as can be confirmed in FIG. 18C, the co-treatment with MβCD and PD induced a remarkable increase in colocalization of GFP-LC3B puncta with LysoTracker Red fluorescence. These results suggest that the lysosomal cholesterol accumulation causes a defect in the autophagosome-lysosome fusion, contributing to the PD-mediated impairment of autophagy flux.

Experimental Result 19. MβCD Restores PD-Mediated Inhibition of Cell Viability.

The effects of cholesterol depletion on the PD-mediated GBM cell death were evaluated by WST1 assay. As can be confirmed in FIG. 19A, it was found that the treatment with 10 μM PD for 3 days reduced the viability of GBM cells, but the combined treatment with MβCD and PD significantly restored the viability of GBM cells.

Figure 19A:
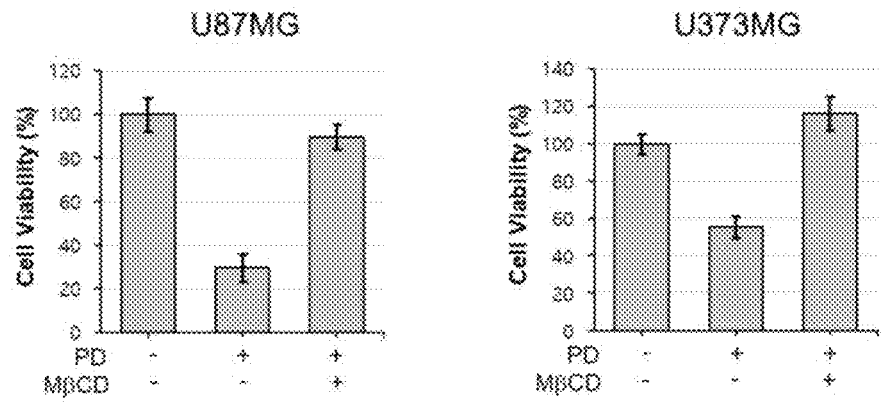
FIGS. 19A and 19B show the results that MβCD restores PD-mediated decrease in cell viability.
Figure 19B:
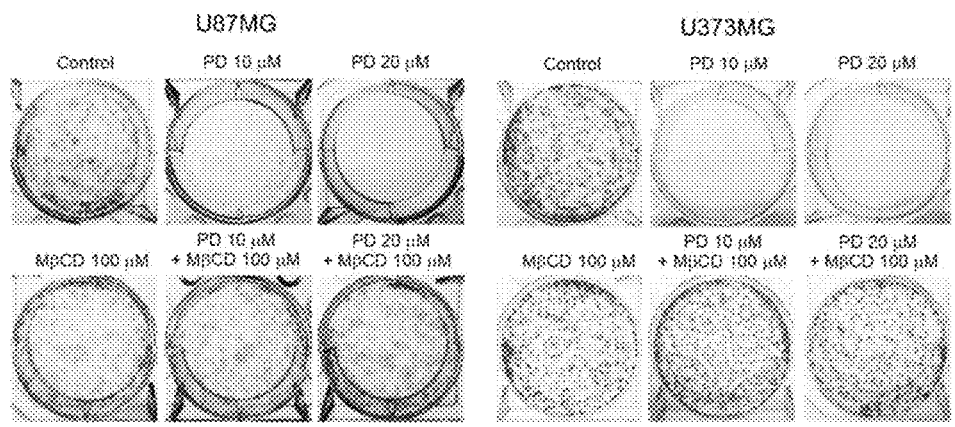

Furthermore, as can be confirmed in FIG. 19B, a colony formation assay was performed to confirm the effects of MβCD on PD-mediated GBM cell death. PD treatment abolished the colony-forming ability of GBM cells, but the colony-forming ability was almost completely recovered by co-treatment with MβCD. These results suggest that cholesterol accumulation is critical for the PD-mediated inhibition of cell viability in GBM cells.

Experimental Result 20. LDLR Upregulation Contributes to PD-Mediated Inhibition of Autophagy and Viability of GBM Cells.

The present inventors hypothesized that the enhanced expression of LDLR and uptake of exogenous cholesterol by PD may promote accumulation of cholesterol in lysosomes and contribute to PD-mediated inhibition of autophagy and cell viability in GBM cells. To this end, the expression of LDLR gene was silenced in GBM cells using lentiviral shRNA transduction.

As can be confirmed in FIG. 19A, the knockdown of LDLR in GBM cells prevented the upregulation of LC3-II and p62 as well as the inactivation of cathpsin B in response to PD in GBM cells. Furthermore, as can be confirmed in FIG. 19B, PD was less effective in reducing cell viability in LDLR-silenced GBM cells. These results demonstrate that the increase in the LDLR expression upon PD treatment contributes to PD-mediated inhibition of autophagic flux and cell viability in GBM cells.

Inhibitory Effects of Extract of *Scutellaria baicalensis*, *Phellodendron amurense* Ruprecht, or *Rubus coreanus*, and a Fraction Thereof Against Glioblastoma Multiforme (GBM)

EXAMPLE 1

Herbal Medicine Materials, Antibodies, and Reagents

Extracts of herbal medicine materials were provided by Hanpoong pharmaceutical company and they were complied with the test regulations for herbal medicine raw materials. The extraction method was used such that an extract was obtained from a 30% ethanol solution, and all the alcohol in the extract was removed using a vacuum concentrator, and then freeze-dried to separate the extracted powder. The obtained powder was dissolved in tertiary distilled water at a concentration of 200 mg/mL and used as a stock.

EXAMPLE 2

Cell Culture

The U87MG glioblastoma multiforme (GBM) and human embryonic kidney cells 293T (HEK293T) used in this experiment were distributed by the Korea Cell Line Bank (located in Seoul National University College of Medicine, Cancer Research Institute).

U87MG and HEK293T cells were cultured in a cell incubator, where a temperature of 37° C. and 5% $CO_2$ are maintained, using a cell culture medium in which 10% fetal bovine serum (FBS) and 1% antibiotic (penicillin and streptomycin; P/S) were added to Dulbecco's Modified Eagle's Medium (DMEM).

EXAMPLE 3

Reverse Transcriptase Polymerase Chain Reaction (RT-PCR)

After deletion of the expression of Ax1 using lentiviral shAx1 in cells, RT-PCR was performed to confirm the deletion. The cells were plated in a 6-well plate at a density of $5\times10^5$ cells/mL, and on the next day, the cells were transferred to each of a culture medium containing shNS (non-specific) and a culture medium containing shAx1 lentiviral particles and cultured for 24 hours, and treated with puromycin for 2 days at a concentration of 1 μg/mL to remove cells not infected with the virus. RNA was isolated from the survived cells using the R&A-Blue total RNA extraction kit, and cDNA was synthesized using the PrimeScript 1st strand cDNA Synthesis kit. Then, RT-PCR was performed using the Maxime PCR Premix kit, GAPDH, and Ax1 primers.

EXAMPLE 4

Western Blot

Cells were washed with PBS and dissolved using a RIPA buffer (150 mM NaCl, 1% NP-40, 0.5% DOC, 0.1% SDS, 50 mM Tris (pH 8.0), 1 mM EDTA, 1 mM PMSF, 1 mM NaF, 1 mM $Na_3PO_4$, 1 μL aprotinin, leupeptin, and pepstatin), and proteins were isolated by centrifugation at 3,000× g for 20 minutes. An equal amount (20 μg) of each of the proteins was separated by 10% sodium dodecyl sulfate-polyacrylamide gel electrophoresis (SDS-PAGE) and the proteins separated using the Trans-blot unit were transferred to a nitrocellulose (NC) membrane. The membrane to which proteins were transferred was blocked with 5% non-fat dry milk (Tris buffered saline (TBS-T) containing 0.1% Tween-20) at room temperature for 1 hour, and primary antibodies, which were diluted at a 1:1,000 concentration, were allowed to react the proteins at 4° C. for 16 hours. After washing with PBS, the resultant was allowed to react with secondary antibodies, which were diluted at a 1:5,000 concentration, at room temperature for 1 hour. A Pierce ECL Western Blotting Substrate, which also underwent a washing process, was coated onto the membrane and allowed to react in a dark room with a film, and thereby, specific protein bands were confirmed.

EXAMPLE 5

MTT Assay

Cells were plated on a 96-well plate at a density of $5 \times 10^4$ cells/mL. On the next day, the cells were treated with an extract of a herbal medicine material at a concentration of 500 μg/mL for 48 hours. The MTT reagent (0.5 mg/mL) was aliquoted to each well in an amount of 200 μL and the cells were again cultured at 37° C. for 2 hours. Then, the MTT reagent was removed and DMSO was seeded to each well in an amount of 200 μL to dissolve all formed formazan, and the absorbance at 540 nm was measured using an ELISA reader.

EXAMPLE 6

Lentiviral shRNA Production

HEK293T cells were plated on a 6-well plate at a density of $1 \times 10^6$ cells/mL. On the next day, 1 μg of pLKO.1/shNS or pLKO.1/shAx1, 0.75 μg of psPAX2 (packaging plasmid), and 0.25 μg of pDM2.G (envelope plasmid) were delivered into the cells using the Lipofectamine 3000 reagent through the liposome-mediated gene transfer method. At time-points of day 2 and day 3 after the gene transfer, respectively, 2 mL of the cell culture was collected and the cells were filtered using a 0.4 μm syringe filter. Then, the filtrates were stored in the refrigerator until they were treated to cells.

Experimental Result 1. Inhibition of Growth of Glioblastoma Multiforme (GBM) by Deletion of Ax1

Since Ax1 is known to have a very important role in cancer cell growth and anticancer drug resistance in almost all kinds of cancer, in order to examine the effects of the deletion of Ax1 expression on brain cancer cell growth, first, the expression of Ax1 was deleted in U87MG and U373MG cells using lentiviral shRNA. The infected U87MG and U373MG cells were each inoculated into a 96-well plate at a density of $5 \times 10^4$ cells/mL after 5 days, and the cells were cultured for 48 hours, followed by an MTT assay.

Figure 22:
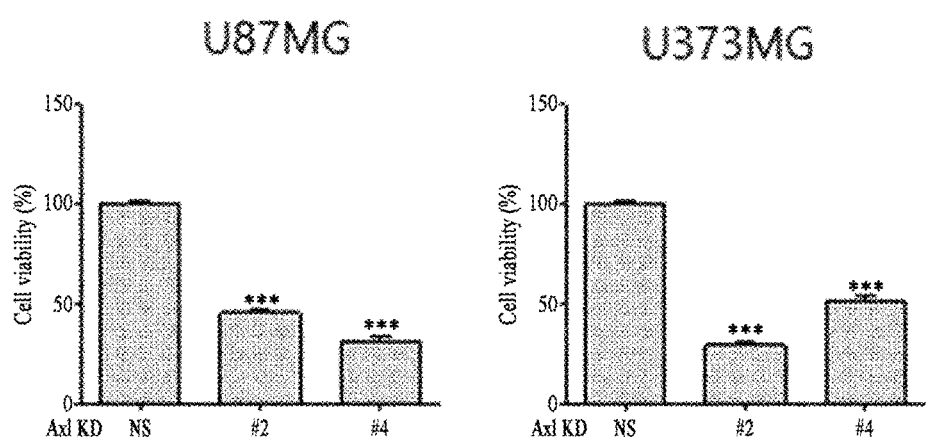
FIG. 22 shows the graphs in which the effect of Ax1 on the growth of GBM was compared by MTT assay by deleting the Ax1 gene in U87MG and U373MG cells (i.e., GBM cell lines) through shRNA.

As a result, as shown in FIG. 22, U87MG and U373MG cells in which the Ax1 expression was deleted showed cell growth rates of 50% or less in both shAx1 #2 and shAx1 #4, compared to the control cells. Through these results, it was found that the expression of Ax1 is very important in the growth of glioblastoma multiforme (GBM).

Experimental Result 2. Changes in Cell Signaling System With Regard to Growth of Glioblastoma Multiforme (GBM) by Deletion of Ax1

The expressions of ERK, p38, JNK1, AKT, S6K, and STAT3 were analyzed so as to examine through which cell signaling pathway the Ax1 deletion inhibits the growth of glioblastoma multiforme (GBM). ERK, p38, JNK1, AKT, S6K, and STAT3 are representative signaling systems closely associated with cancer cell growth.

Therefore, the degree of phosphorylation of each of the proteins showing the respective activity of ERK, p38, JNK1, AKT, S6K, and STAT3 in the U87MG and U373MG cells, in which the Ax1 is deleted, was confirmed by western blotting.

Figure 23:
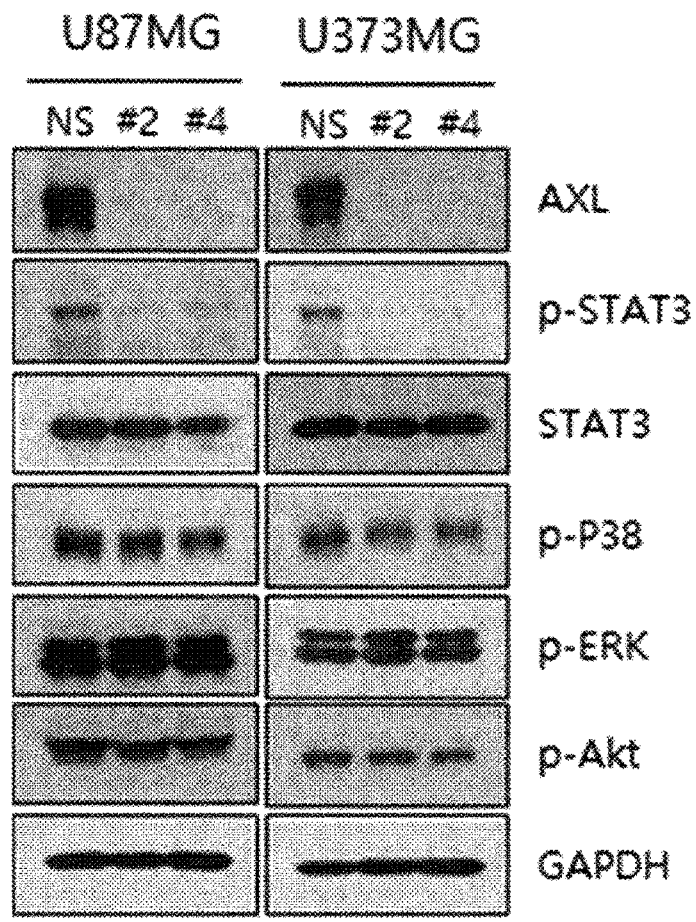
FIG. 23 shows the results in which western blot was performed so as to analyze which mechanism was inhibited in U87MG and U373MG cells (i.e., GBM cell lines), in which the Ax1 gene is deleted, thereby leading to the inhibition of GBM growth.

As a result, as shown in FIG. 23, it was found that only the activity of STAT3 was decreased by the Ax1 deletion in the same manner in both U87MG and U373MG cells and other signaling systems remained unchanged. Through these results, it was confirmed that the deletion of Ax1 inhibits the growth of glioblastoma multiforme (GBM) by reducing the activity of STAT3.

Experimental Result 3. Screening of Herbal Medicine Materials Reducing Expression Level of Ax1 Protein Through the above process, it was confirmed that the decrease in the Ax1 expression of glioblastoma multiforme (GBM) results in inhibition of the growth of GBM. Therefore, in order to find herbal medicine materials that can reduce the Ax1 expression, the water extracts of 26 different kinds of herbal medicine materials were each treated on a U87MG cell line (i.e., a representative GBM cell line) and the level of Ax1 expression was confirmed by western blotting. Specifically, the water extracts of herbal medicine materials were each treated at a concentration of 500 μg/mL for 24 hours. Proteins were extracted from the U87MG cell line treated with herbal medicine materials, subjected to western blotting was performed, and the expression level of GAPDH was confirmed as a control for correcting the Ax1 overexpression.

As a result, as shown in FIG. 24, it was found that the treatment of each extract of *Rubus coreanus*, *Trichosanthes kirilowii*, *Scutellaria baicalensis*, or *Phellodendron amurense* Ruprecht reduced the thickness of protein bands. Through these results, it was confirmed that *Rubus coreanus*, *Trichosanthes kirilowii*, *Scutellaria baicalensis*, or *Phellodendron amurense* Ruprecht inhibits and reduces the expression of Ax1 and thus can be a herbal medicine material capable of treating glioblastoma multiforme (GBM).

Experimental Result 4. Inhibitory Effect of Extract of *Phellodendron amurense* Ruprecht or *Scutellaria baicalensis* Against Growth of Glioblastoma Multiforme (GBM)

In order to examine what role is played by the extract of *Phellodendron amurense* Ruprecht or *Scutellaria baicalensis*, in which the ability of deleting Ax1 expression is confirmed, on the growth of U87MG (i.e., a representative GBM cell line), U87MG cells were plated on a 96-well plate at a density of $5 \times 10^4$ cells/mL. On the next day, the *Phellodendron amurense* Ruprecht extract was treated at a concentration of 500 μg/mL for 48 hours and the *Scutellaria baicalensis* extract was treated at a concentration of 20 μg/mL to 1,000 μg/mL for 48 hours, followed by an MTT assay.

As a result, as shown in FIG. 25, the U87MG cells cultured in a cell culture medium containing a *Phellodendron amurense* Ruprecht extract (500 μg/mL) showed a cell growth rate of about 65% compared to the control group, and as shown in FIG. 26, and the U87MG cells cultured in a cell culture medium containing a *Scutellaria baicalensis* extract (1,000 μg/mL) showed a cell growth rate of about 30% compared to the control group.

Through these results, it was confirmed that the *Scutellaria baicalensis* or *Phellodendron amurense* Ruprecht extract has the abilities of inhibiting the expression of Ax1 in U87MG cells and inhibiting the growth of GBM.

Experimental Result 5. Changes in Cell Signaling System of Glioblastoma Multiforme (GBM) by Extract of *Phellodendron amurense* Ruprecht and *Scutellaria baicalensis*

In Experimental Result 2 above, it was confirmed that the activity of STAT3 in the signaling system is reduced in glioblastoma multiforme (GBM), in which the Ax1 is deleted. Through which cell signaling pathway the growth of cancer cells is inhibited by the *Phellodendron amurense* Ruprecht or *Scutellaria baicalensis* extract was confirmed by western blotting.

The *Phellodendron amurense* Ruprecht or *Scutellaria baicalensis* extract was treated on U87MG cells at a concentration of 500 μg/mL for 48 hours, and the degree of phosphorylation of each of the proteins showing the respective activity of ERK, p38, JNK1, AKT, S6K, and STAT3 in the U87MG cells was confirmed by western blotting.

Figure 27:
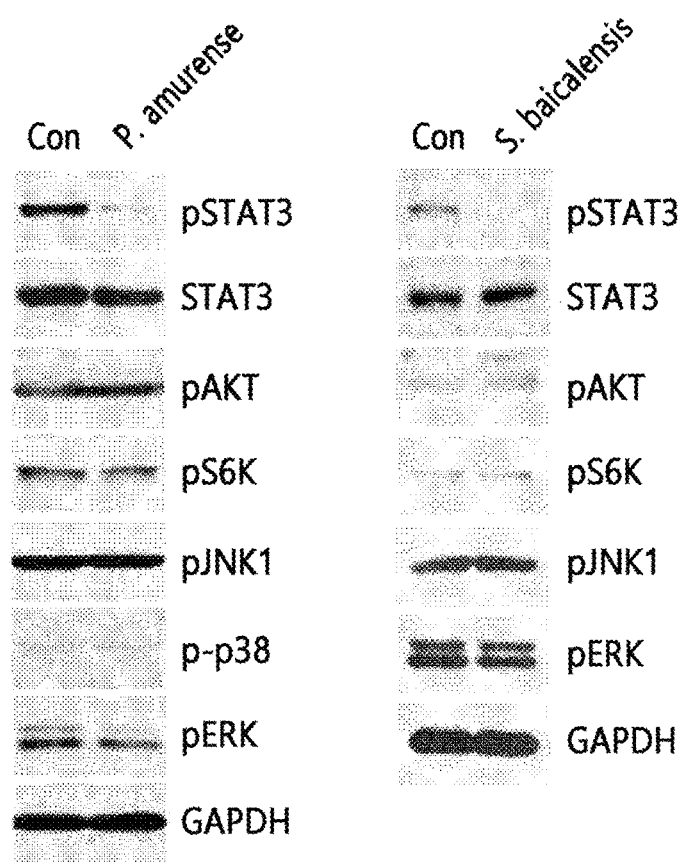
FIG. 27 shows the results in which western blot was performed so as to analyze which mechanism was inhibited in *Scutellaria baicalensis* and *Phellodendron amurense* Ruprecht (which have shown the effect of inhibiting the growth of GBM), thereby leading to the inhibition of GBM growth.

As a result, as shown in FIG. 27, it was confirmed that when the *Phellodendron amurense* Ruprecht or *Scutellaria baicalensis* extract was treated on U87MG cells at a concentration of 500 μg/mL for 48 hours, the activity of STAT3 was rapidly decreased while there were no changes in other signaling systems. Through these results, it was confirmed that the *Phellodendron amurense* Ruprecht or *Scutellaria baicalensis* extract inhibits the growth of GBM by reducing the activity of STAT3, and it was confirmed that the inhibition of the growth of GBM is an effect similar to the inhibition of an activity through viral infection.

Experimental Result 6. Confirmation of Natural Compounds Inducing Ax1 Deletion in Malignant Glioblastoma Multiforme (GBM)

To discover natural compounds capable of inducing the deletion of Ax1 expression, baicalein, berberin, wogonin, quercetin, and baicalin (i.e., the representative natural compounds of *Phellodendron amurense* Ruprecht, *Scutellaria baicalensis*, and *Rubus coreanus*) were treated on U87MG and U373MG cells at varying concentrations for 48 hours, and the presence/absence of deletion of Ax1 was confirmed by western blot.

As a result, it was observed that baicalin (which is contained in both *Phellodendron amurense* Ruprecht and *Phellodendron amurense* Ruprecht) and quercetin (i.e., a representative natural compound of *Rubus coreanus*) reduced the expression of Ax1 in both U87MG and U373MG cells.

Conclusively, in the present invention, herbal medicine materials targeting Ax1 of glioblastoma multiforme (GBM) were discovered and these medicine materials were suggested as candidate natural anticancer drugs for GBM.

Based on previous study results that Ax1 has an important role in the growth of cancer cells and it reduces the growth of cancer cells when treated with Ax1 inhibitors, the effects of the deletion of Ax1 on the growth of GBM was examined. As a result, it was confirmed that the deletion of Ax1 by lentiviral shRNA inhibited the growth of U87MG and U373MG to a level of 50% or less, and through these results, it was confirmed that Ax1 also has an important role in the growth of GBM.

Additionally, the extract of *Phellodendron amurense* Ruprecht, *Scutellaria baicalensis*, or *Rubus coreanus* was shown to reduce the expression of Ax1 protein, thus suggesting a possibility that these extracts may be used for the treatment of GBM. Among them, the extract of *Phellodendron amurense* Ruprecht or *Scutellaria baicalensis* was shown to inhibit the growth of cancer cells in cell lines and inhibit the activity of STAT3 by reducing the expression of Ax1 protein, thus eventually capable of inhibiting the growth of GBM.

Through these results, it was suggested that not only the extract of *Phellodendron amurense* Ruprecht, *Scutellaria baicalensis*, or *Rubus coreanus* can be effectively used for the treatment of GBM, but also Ax1 can be a novel efficient target with regard to the treatment of GBM.

From the foregoing, one of ordinary skill in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A method for treatment of glioblastoma multiforme (GBM), which comprises administering a pharmaceutical composition to a subject in need thereof or suffering from GBM or a symptom thereof, wherein
the pharmaceutical composition contains as an active ingredient an extract of *Platycodon grandiflorum*, an extract of *Phellodendron amurense* Ruprecht, an extract of *Scutellaria baicalensis* and *Rubus coreanus*, a fraction thereof, or any combination thereof;
the extracts are obtained from solvent extraction thereof, the solvent optionally being an aqueous, alcoholic, or aqueous alcoholic solvent;
the extract of *Platycodon grandiflorum*, the extract of *Phellodendron amurense* Ruprecht, or the extract of *Scutellaria baicalensis* and *Rubus coreanus* is present in the pharmaceutical composition in a therapeutically effective amount;
the pharmaceutical composition effects treating said GBM or symptom thereof, via inhibiting GBM growth, inhibiting autophagy in cancer cells, or reducing the expression of Ax1 protein in cancer cells.

2. The method of claim 1, wherein the extract of *Platycodon grandiflorum*, the extract of *Phellodendron amurense* Ruprecht, and the extract of *Scutellaria baicalensis* and *Rubus coreanus* are prepared by hot water extraction.

3. The method of claim 1, wherein the extract of *Platycodon grandiflorum* or a fraction thereof is contained in an amount of 0.01 wt % to 80 wt % relative to the total amount of the composition.

4. The method of claim 1, wherein the extract of *Platycodon grandiflorum* or a fraction thereof comprises platycodin D.

5. The method of claim 4, wherein platycodin D is contained in an amount of 0.01 wt % to 80 wt % relative to the total amount of the composition.

6. The method of claim 1, wherein the extract of *Phellodendron amurense* Ruprecht or the extract of *Scutellaria*

*baicalensis* and *Rubus coreanus* is contained in an amount of 0.0001 wt % to 80 wt % relative to the total amount of the composition.

7. The method of claim 1, wherein the composition further comprises at least any one selected from the group consisting of a pharmaceutically acceptable salt, a carrier, an excipient, and a diluent.

8. The method of claim 1, wherein inhibition of GBM growth is achieved by inhibition of autophagy in cancer cells.

9. The method of claim 1, wherein the inhibition of autophagy increases the expression of a low density lipoprotein receptor (LDLR) in cancer cells.

\* \* \* \* \*

SEQUENCE LISTING

```
<160> NUMBER OF SEQ ID NOS: 7

<210> SEQ ID NO 1
<211> LENGTH: 23
<212> TYPE: DNA
<213> ORGANISM: Artificial Sequence
<220> FEATURE:
<223> OTHER INFORMATION: human SQSTM1-forward

<400> SEQUENCE: 1
gaactccagt ccctacagat gcc                                          23

<210> SEQ ID NO 2
<211> LENGTH: 20
<212> TYPE: DNA
<213> ORGANISM: Artificial Sequence
<220> FEATURE:
<223> OTHER INFORMATION: human SQSTM1-reverse

<400> SEQUENCE: 2
cgggagatgt gggtacaagg                                              20

<210> SEQ ID NO 3
<211> LENGTH: 19
<212> TYPE: DNA
<213> ORGANISM: Artificial Sequence
```

```
<220> FEATURE:
<223> OTHER INFORMATION: human LDLR-forward

<400> SEQUENCE: 3
cagatatcat caacgaagc                                                 19

<210> SEQ ID NO 4
<211> LENGTH: 21
<212> TYPE: DNA
<213> ORGANISM: Artificial Sequence
<220> FEATURE:
<223> OTHER INFORMATION: human LDLR-reverse

<400> SEQUENCE: 4
cctctcacac cagttcactc c                                              21

<210> SEQ ID NO 5
<211> LENGTH: 20
<212> TYPE: DNA
<213> ORGANISM: Artificial Sequence
<220> FEATURE:
<223> OTHER INFORMATION: human GAPDH-forward

<400> SEQUENCE: 5
cgtcttcacc accatggaga                                                20

<210> SEQ ID NO 6
<211> LENGTH: 20
<212> TYPE: DNA
<213> ORGANISM: Artificial Sequence
<220> FEATURE:
<223> OTHER INFORMATION: human GAPDH-reverse

<400> SEQUENCE: 6
cggccatcac gccacagttt                                                20

<210> SEQ ID NO 7
<211> LENGTH: 19
<212> TYPE: DNA
<213> ORGANISM: Artificial Sequence
<220> FEATURE:
<223> OTHER INFORMATION: shLDLR

<400> SEQUENCE: 7
ccacttgtag gagatgcat                                                 19
```